US006960458B2

(12) United States Patent
Ookura et al.

(10) Patent No.: US 6,960,458 B2
(45) Date of Patent: Nov. 1, 2005

(54) ERYTHROSE REDUCTASE, ITS CDNA AND CELL WHICH THE CDNA EXPRESS

(75) Inventors: Tetuya Ookura, Tsukuba (JP); Takafumi Kasumi, Ushiku (JP); Eiji Asaba, Omiya (JP)

(73) Assignee: Director of National Food Research Institute, Ministry of Agriculture, Forestry and Fisheries, Tsukuba (JP)

( * ) Notice: Subject to any disclaimer, the term of this patent is extended or adjusted under 35 U.S.C. 154(b) by 510 days.

(21) Appl. No.: 10/040,416

(22) Filed: Jan. 9, 2002

(65) Prior Publication Data

US 2002/0160480 A1 Oct. 31, 2002

Related U.S. Application Data

(63) Continuation-in-part of application No. 09/800,487, filed on Mar. 8, 2001, now abandoned.

(30) Foreign Application Priority Data

Jan. 9, 2001 (JP) ........................................ 2001-001294

(51) Int. Cl.[7] ............................ C12N 9/02; C12N 15/00; C12N 1/20; C12P 7/02; C07H 21/04
(52) U.S. Cl. ................. 435/189; 435/252.2; 435/320.1; 435/4; 435/6; 435/25; 435/155; 435/69.1; 536/23.2; 536/23.74
(58) Field of Search ............................ 435/189, 252.3, 435/320.1, 4, 6, 25, 155, 69.1, 71.1; 536/23.2

(56) References Cited

FOREIGN PATENT DOCUMENTS

| JP | 4-635 | 1/1992 |
|---|---|---|
| JP | 4-11189 | 2/1992 |
| JP | 6-30591 | 4/1994 |
| JP | 6-30592 | 4/1994 |
| JP | 9-154589 | 6/1997 |
| JP | 10-96 | 1/1998 |

OTHER PUBLICATIONS

Kita et al. Cloning of the aldehyde reductase gene from a red yeast, Sporobolomyces salmonicolor, and characterization of the gene and its product.Appl Environ Microbiol. Jul. 1996;62(7):2303–10.*

Kohno et al. Purification and properties of beef liver aldehyde reductase catalyzing the reduction of D–erythrose 4–phosphate. J Biochem (Tokyo). Jan. 1985;97(1):79–87.*

K. Tokuoka, et al., J. Gen. Appl. Microbiol., vol. 38, pps. 145–155, "Comparison of Three Forms of Erythrose Reductase from an *Aureobasidium* sp. Mutant", 1992.

H. Ishizuka, et al., Biosci. Biotech. Biochem., vol. 56, No. 6, pps. 941–945, "Purification and Some Properties of an Erythrose Reductase from an *Aureobasidium* sp. Mutant", 1992.

M. J. Zoller, et al., Nucleic Acids Research, vol 10, No. 20, pps. 6487–6501, "Oligonucleotide–Directed Mutagenesis Using M13–Derived Vectors: An Efficient and General Procedure for the Priduction of Point Mutations in any Fragment of DNA", 1982.

(Continued)

*Primary Examiner*—Manjunath Rao
*Assistant Examiner*—Yong Pak
(74) *Attorney, Agent, or Firm*—Oblon, Spivak, McClelland, Maier & Neustadt, P.C.

(57) ABSTRACT

Protein having an erythrose reductase activity; a DNA encoding the protein; a cell to which a DNA has been transferred in a manner such that the DNA is capable of expressing an erythrose reductases type III, II or I the DNA encodes; and a method for producing erythritol, comprising acting the erythrose reductases type III, II or I or a cell to which erythrose reductases type III, II or I has been transferred in a manner capable of expressing the erythrose reductases type III, II or I on D-erythrose and harvesting the produced erythritol.

12 Claims, 8 Drawing Sheets

OTHER PUBLICATIONS

Molecular Cloning, 2$^{nd}$ Edition., pps 14.2 to 14.35, "In Vitro Amplification of DNA by the Polymerase Chain Reaction", 1989.

T. Clackson, et al., PCR, A Practical Approach, pps. 200–209, "General Applications of PCR to Gene Cloning and Manipulation", 1991.

"Fundamental Course on Microbiology 8, Genetic Engineering", pps. 370–375 (with partial English translation).

J. Reiser, et al., Advances In Biochemical Engineering/ Biotechnology, vol. 43, pps. 76–102, "Transfer and Expression of Heterologous Genes in Yeasts Other than *Saccharomyces cerevisiae*", 1990.

M. A. Romanos, et al., Yeast, vol. 8, pps. 423–488, "Foreign Gene Expression in Yeast: A Review", 1992.

H. Hirano, Journal of Protein Chemistry, vol. 8, No. 1, pps. 115–130, "Microsequence Analysis of Winged Bean Seed Proteins Electroblotted from Two–Dimensional Gel", 1989.

* cited by examiner

Biosynthesis of Erythritol from Glucose

FIG. 9

| marker (pI) | ① | ② | ③ | ④ |
|---|---|---|---|---|
| 5.85 | | | | |
| 5.20 | | | | |
| 4.55 | | | | |
| 4.15 | | | | |

ERYTHROSE REDUCTASE, ITS CDNA AND CELL WHICH THE CDNA EXPRESS

This application is a continuation-in-part of Ser. No. 09/800,487, filed Mar. 8, 2001, now abandoned.

FIELD OF THE INVENTION

The present invention relates to a novel protein having an erythrose reductase activity, to a complementary DNA encoding the protein, to a method for producing a protein possessing an erythrose reductase activity, and to a method for producing erythritol.

The erythrose reductase is an enzyme that reduces erythrose with NADPH or NADH for producing erythritol and $NADP^+$ or $NAD^+$. The enzyme includes three kinds of isozymes, i.e., type I, type II and type III classified after differences in mobility on Native-PAGE and isoelectric focusing electrophoresis.

BACKGROUND OF THE INVENTION

Erythritol is a high quality and very low-calorie sweetness. Erythritol is also noncariotic so that it is widely used as a sweetener for food and beverage.

Several microorganisims such as *Trichosporonoides* and *Moniliella* are widely used for industrial production of erythritol from glucose. Microorganisms such as those belonging to the genera *Trichosporonoides, Moniliella,* etc., are caused to act on a substrate such as glucose (cf. Japanese Patent Publication No. Hei 6-30591, Japanese Patent Publication No. Hei 6-30592, Japanese Patent Publication No. Hei 4-11189, Japanese Patent Publication No. Hei 4-635, Japanese Patent Kokai No. Hei 10-96, and Japanese Patent Kokai No. Hei 9-154589).

It has been reported that erythrose reductase type I, II and III are involved in producing eythritol at *Trichosporonoides megachiliensis* Strain SN-G42 (FERM BP-1430) (K. Tokuoka, et al., J. Gen. Appl. Microbiol., 38, 145–155 (1992)).

The metabolic pathway from glucose to erythritol in *Trichosporonoides megachiliensis* Strain SN-G42 is illustrated in FIG. 1.

As illustrated in FIG. 1, glucose enters the Pentose Phosphate Shunt to produce erythrose-4-phosphate (Erythrose-4-P) after this sugar phosphate is metabolited to glucose-6-phosphate (Glc-6-P) or glyceraldehyde-3-phosphate by glycolysis.

The erythrose-4-phosphate is dephosphorylated to produce D-erythrose and D-erythrose, which gets reduction by NADPH or NADH to produce meso-eythritol.

Of such a series of reactions, the erythrose reductase type I, II and III all catalyze the latter reductive reaction (i.e., the reaction in which erythrose gets reduction by NADPH or NADH to form meso-eythritol).

The reports on erythrose reductases only described their enzymological properties. The genetical analysis of these enzymes remains to be elucidated.

An object of the present invention is to provide an efficient method for the production of erythritol.

Another object of the present invention is to clarify the primary structures of enzyme having an erythrose reductase activity and to characterize a complementary DNA encoding the protein in order to establish an erythritol producing microorganism and to provide a method for utilizing them.

If it is successful in obtaining the DNA that encodes the protein having an erythrose reductase activity, a large amount of proteins can be produced by expressing the DNA in a cell such as *Esherichia coli*, yeast cell, etc., or the like means. This invention not only leads to mass production of erythritol but also is applied to development of mutant enzymes having higher erythritol productivity, cloning of DNA encoding related enzymes and the like by using genetic engineering techniques.

SUMMARY OF THE INVENTION

The present inventors have made extensive research with view to achieving the above-described object and as a result, they have found a base sequence of DNA encoding a protein having an erythrose reductase activity. Said protein is produced by a microorganism belonging to the genus *Trichosporonoides*.

That is, the present inventors have first harvested an enzyme from the microorganism and purified it, partially decoding the amino acid sequence of a protein of the first aspect of the present invention, said protein having an erythrose reductase activity is produced by the microorganism belonging to the genus *Trichosporonoides* by peptide mapping, and preparing a probe based thereon.

By performing Northern hybridization of erythritol producing microorganism using this probe, the time when erythrose reductase type III highly expressed was identified. A cDNA library was prepared from mRNA at the time when expression level is highest.

Then, the cDNA library was screened with the above-described probe and the base sequence of DNA of a protein having an erythrose reductase activity was decoded.

Subsequently, the cDNA library was screened with the above-described probe, and the base sequence of DNA of a protein having an erythrose reductase activity was decoded.

Moreover, the present inventors prepared a probe based on full-length cDNA of the above obtained erythrose reductase of the first aspect of the present invention, and performed screening by carrying out hybridization using the above-described cDNA library under the conditions described in item (b) of claim 3 and in claim 4, or in item (d) of claim 5 and in claim 6. As a result, base sequences of DNA of proteins having erythrose reductase activity of the second or a third aspect of the present invention were decoded.

Furthermore, using this screened cDNA, it was incorporated into an *Escherichia coli* expression vector, and a protein having an erythrose reductase activity was expressed as a histidine Tag-fused protein in *Escherichia coli*.

The activity, substrate specificity, and the like of the thus-obtained recombinant protein were examined and as a result, it was confirmed that the recombinant protein had a substrate specificity similar to that of natural type erythrose reductase and also had an enzyme activity of producing a sugar alcohol.

Moreover, it was also confirmed that the introduction of a plasmid into auxotrophic yeast induced accurate expression.

The present invention has been completed based on these findings.

That is, in a first embodiment, the present invention provides a protein shown in (A) or (B) below:
(A) a protein having an amino acid sequence of SEQ. ID No. 2 in the Sequence Listing;
(B) a protein having an amino acid sequence of SEQ. ID No. 2 in the Sequence Listing, wherein the amino acid sequence includes substitution, deletion, insertion, addition or inversion of one or several amino acids and wherein the protein has an erythrose reductase activity.

In a second embodiment, the present invention provides a DNA encoding a protein shown in (A) or (B) below:
(A) a protein having an amino acid sequence of SEQ. ID No. 2 in the Sequence Listing;
(B) a protein having an amino acid sequence of SEQ. ID No. 2 in the Sequence Listing, wherein the amino acid sequence includes substitution, deletion, insertion, addition or inversion of one or several amino acids and wherein the protein has an erythrose reductase activity.

In a third embodiment, the present invention provides the DNA as described in the above second embodiment, wherein the DNA comprises one shown in (a) or (b) below:
(a) a DNA containing a base sequence comprising at least nucleotides Nos. 1 to 399 out of the nucleotide sequence described in SEQ. ID No. 1 in the Sequence Listing.
(b) a DNA hybridizing with a base sequence comprising at least nucleotides Nos. 1 to 399 out of the nucleotide sequence described in SEQ. ID No. 1 in the Sequence Listing or a probe prepared therefrom under a stringent condition and encoding a protein having an erythrose reductase activity.

In a fourth embodiment, the present invention provides the DNA as described in the above third embodiment, wherein the stringent condition is a condition under which washing is performed at a salt concentration corresponding to 2×SSC containing 0.1% SDS at 60° C.

In a fifth embodiment, the present invention provides the DNA as described in the above second embodiment, wherein the DNA comprises a DNA shown in (c) or (d) below:
(c) a DNA containing a base sequence comprising at least nucleotides Nos. 408 to 1119 out of the nucleotide sequence described in SEQ. ID No. 1 in the Sequence Listing.
(d) a DNA hybridizing with a base sequence comprising at least nucleotides Nos. 408 to 1119 out of the nucleotide sequence described in SEQ. ID No. 1 in the Sequence Listing under a stringent condition and encoding a protein having an erythrose reductase activity.

In a sixth embodiment, the present invention provides the DNA as described in the above fifth embodiment, wherein the stringent condition is a condition under which washing is performed at a salt concentration corresponding to 2×SSC containing 0.1% SDS at 60° C.

In a seventh embodiment, the present invention provides a cell to which a DNA as described in any one of the above second to sixth embodiments has been introduced in a manner such that the DNA is capable of expressing an erythrose reductase type III.

In an eighth embodiment, the present invention provides a method for producing erythrose reductase type III, comprising the steps of culturing the cell as described in the above seventh embodiment in a medium to produce and accumulate erythrose reductase type III in a culture liquid and harvesting the erythrose reductase type III from the culture liquid.

In a ninth embodiment, the present invention provides a protein shown in (C) or (D) below:
(C) a protein having an amino acid sequence of SEQ. ID No. 4 in the Sequence Listing;
(D) a protein having an amino acid sequence of SEQ. ID No. 4 in the Sequence Listing, wherein the amino acid includes substitution, deletion, insertion, addition or inversion of one or several amino acids and wherein the protein has an erythrose reductase activity.

In a tenth embodiment, the present invention provides a DNA encoding a protein shown in (C) or (D) below:
(C) a protein having an amino acid sequence of SEQ. ID No. 4 in the Sequence Listing;
(D) a protein having an amino acid sequence of SEQ. ID No. 4 in the Sequence Listing, wherein the amino acid sequence includes substitution, deletion, insertion, addition or inversion of one or several amino acids and wherein the protein has an erythrose reductase activity.

In an eleventh embodiment, the present invention provides the DNA as described in the above tenth embodiment, wherein the DNA comprises one shown in (e) or (f) below:
(e) a DNA containing a base sequence comprising at least nucleotides Nos. 1 to 399 out of the nucleotide sequence described in SEQ. ID No. 3 in the Sequence Listing.
(f) a DNA hybridizing with a base sequence comprising at least nucleotides Nos. 1 to 399 out of the nucleotide sequence described in SEQ ID No. 3 in the Sequence Listing or a probe prepared therefrom under a stringent condition and encoding a protein having an erythrose reductase activity.

In a twelfth embodiment, the present invention provides the DNA as described in the above eleventh embodiment, wherein the stringent condition is a condition under which washing is performed at a salt concentration corresponding to 2×SSC containing 0.1% SDS at 60° C.

In a thirteenth embodiment, the present invention provides the DNA as described in the above tenth embodiment, wherein the DNA comprises a DNA shown in (g) or (h) below:
(g) a DNA containing a base sequence comprising at least nucleotides Nos. 408 to 1077 out of the nucleotide sequence described in SEQ. ID No. 3 in the Sequence Listing.
(h) a DNA hybridizing with a base sequence comprising at least nucleotides Nos. 408 to 1077 out of the nucleotide sequence described in SEQ. ID No. 3 in the Sequence Listing under a stringent condition and encoding a protein having an erythrose reductase activity.

In a fourteenth embodiment, the present invention provides the DNA as described in the above thirteenth embodiment, wherein the stringent condition is a condition under which washing is performed at a salt concentration corresponding to 2×SSC containing 0.1% SDS at 60° C.

In a fifteenth embodiment, the present invention provides a cell to which a DNA as described in any one of the above tenth to fourteenth embodiments has been introduced in a manner such that the DNA is capable of expressing an erythrose reductase type II.

In an sixteenth embodiment, the present invention provides a method for producing erythrose reductase type II, comprising the steps of culturing the cell as described in the above fifteenth embodiment in a medium to produce and accumulate erythrose reductase type II in a culture liquid and harvesting the erythrose reductase type II from the culture liquid.

In a seventeenth embodiment, the present invention provides a protein shown in (E) or (F) below:
(E) a protein having an amino acid sequence of SEQ. ID No. 6 in the Sequence Listing;
(F) a protein having an amino acid sequence of SEQ. ID No. 6 in the Sequence Listing, wherein the amino acid sequence includes substitution, deletion, insertion, addition or inversion of one or several amino acids and wherein the protein has an erythrose reductase activity.

In an eighteenth embodiment, the present invention provides a DNA encoding a protein shown in (E) or (F) below:
(E) a protein having an amino acid sequence of SEQ. ID No. 6 in the Sequence Listing;
(F) a protein having an amino acid sequence of SEQ. ID No. 6 in the Sequence Listing, wherein the amino acid sequence includes substitution, deletion, insertion, addition or inversion of one or several amino acids and wherein the protein has an erythrose reductase activity.

In a nineteenth embodiment, the present invention provides the DNA as described in the above eighteenth embodiment, wherein the DNA comprises one shown in (i) or (j) below:
(i) a DNA containing a base sequence comprising at least nucleotides Nos. 1 to 399 out of the nucleotide sequence described in SEQ. ID No. 5 in the Sequence Listing.
(j) a DNA hybridizing with a base sequence comprising at least nucleotides Nos. 1 to 399 out of the nucleotide sequence described in SEQ. ID No. 5 in the Sequence Listing or a probe prepared therefrom under a stringent condition and encoding a protein having an erythrose reductase activity.

In a twentieth embodiment, the present invention provides the DNA as described in the above nineteenth embodiment, wherein the stringent condition is a condition under which washing is performed at a salt concentration corresponding to 2×SSC containing 0.1% SDS at 60° C.

In a twenty first embodiment, the present invention provides the DNA as described in the above eighteenth embodiment, wherein the DNA comprises a DNA shown in (k) or (l) below:
(k) a DNA containing a base sequence comprising at least nucleotides Nos. 408 to 1121 out of the nucleotide sequence described in SEQ. ID No. 5 in the Sequence Listing.
(l) a DNA hybridizing with a base sequence comprising at least nucleotides Nos. 408 to 1121 out of the nucleotide sequence described in SEQ. ID No. 5 in the Sequence Listing under a stringent condition and encoding a protein having an erythrose reductase activity.

In a twenty second embodiment, the present invention provides the DNA as described in the above twenty first embodiment, wherein the stringent condition is a condition under which washing is performed at a salt concentration corresponding to 2×SSC containing 0.1% SDS at 60° C.

In a twenty third embodiment, the present invention provides a cell to which a DNA as described in any one of the above eighteenth to twenty second embodiments has been introduced in a manner such that the DNA is capable of expressing an erythrose reductase type I.

In an twenty fourth embodiment, the present invention provides a method for producing erythrose reductase type I, comprising the steps of culturing the cell as described in the above twenty third embodiment in a medium to produce and accumulate erythrose reductase type I in a culture liquid and harvesting the erythrose reductase type I from the culture liquid.

In a twenty fifth embodiment, the present invention provides a method for producing erythritol, comprising the steps of acting a protein having an erythrose reductase activity as described in any one of the above first or ninth or seventeenth embodiment on D-erythrose and harvesting a produced erythritol.

In a twenty sixth embodiment, the present invention provides a method for producing erythritol, comprising the steps of acting the cell as described in any one of the above seventh or fifteenth or twenty third embodiment on D-erythrose and harvesting a produced erythritol.

BRIEF DESCRIPTION OF THE DRAWINGS

FIG. 9 is an electrophoretogram showing the results of IEF-PAGE on erythrose reductase, wherein Lane 1 shows the isoelectric point marker protein, Lane 2 shows the result on the purified recombinant erythrose reductase type I, Lane 3 shows the result on the purified recombinant erythrose reductase type II, and Lane 4 shows the result on the purified recombinant erythrose reductase type III.

DETAILED DESCRIPTION OF THE INVENTION

Figure 1:
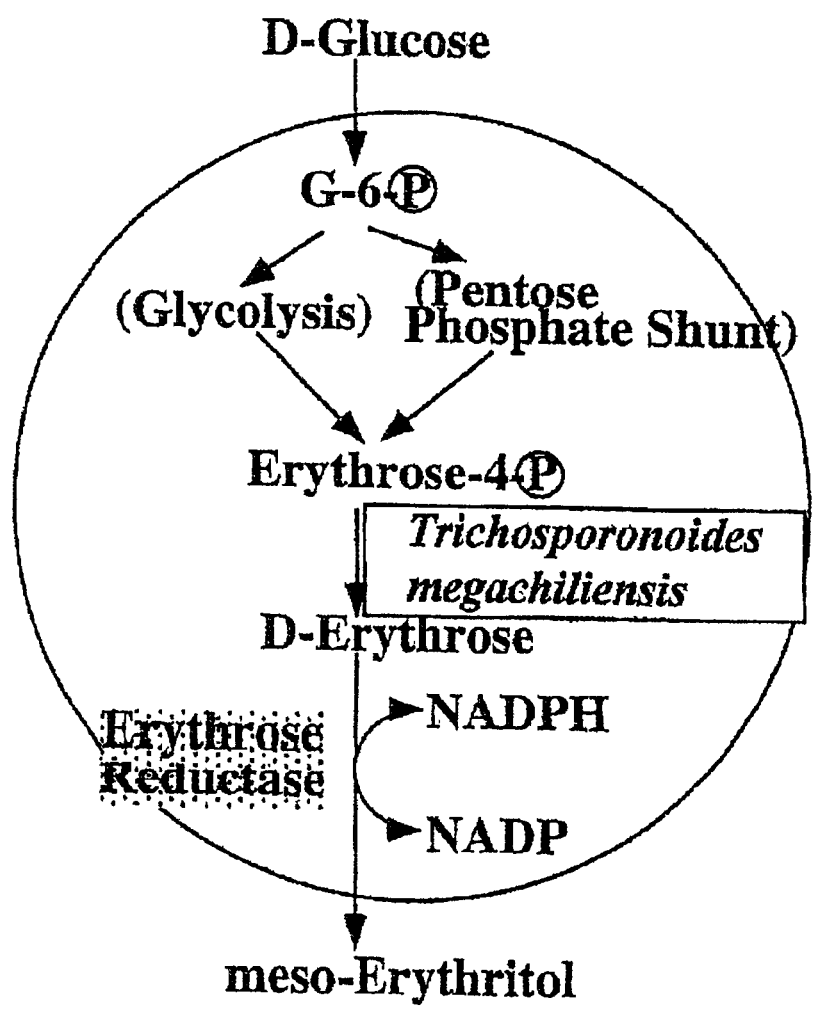
FIG. 1 is a schematic diagram illustrating erythritol biosynthesis pathway.

Hereinafter, the present invention will be described in detail.

The protein having an erythrose reductase activity of the present invention exists in yeast belonging to the genus *Trichosporonoides* which is an erythritol producing microorganism. *Trichosporonoides megachiliensis* is a typical yeast.

Firstly, description will be made about obtaining of DNA encoding a protein having an erythrose reductase activity of the first aspect of the present invention.

In the first aspect of the present invention, the DNA encoding a protein having an erythrose reductase activity can be prepared, for example, by purifying a protein having an enzyme activity obtained from an erythritol producing microorganism, partially decoding an amino acid sequence of the protein, preparing a probe based on the partially decoded amino acid sequence, and then screening the cDNA library of the above-described microorganism using the probe, as established by the present inventors.

The present inventors first obtained erythrose reductase type III from an erythritol producing microorganism by a conventional process in order to prepare a probe for screening, purified the enzyme and then decoded the amino acid sequence of the protein.

To obtain erythrose reductase type III from the *Trichosporonoides megachiliensis* Strain SN-G42, the procedures described in H. Ishizuka, et al., Biosci. Biotech. Biochem., 56(6), 941–945, 1992 may be employed.

There can be used not only this procedure but also usual procedure for obtaining and purifying protein with a combination of centrifugal separation, dialysis, various kinds of chromatographies, etc.

The partial amino acid sequence from the purified erythrose reductase type III can be obtained by peptide mapping by a conventional method after digestion.

The amino acid sequence can be determined by Edman degradation and use of an automatic amino acid sequencer makes the determination more convenient.

Next, the present inventors carried out PCR reaction using a primer designed from the partially decoded amino acid sequence and the cDNA from erythritol producing microorganism as a template to prepare a probe.

The design of a primer based on the partially decoded amino acid sequence can be performed by a conventional method.

For example, referring to the amino acid sequences of the aldo-keto reductase families, parts of the partially decoded amino acid (cf. SEQ. ID Nos. 9 and 10 in the Sequence Listing) can be selected and sense primers and anti-sense primers (cf. SEQ. ID Nos. 7 and 8 in the Sequence Listing) can be designed from the respective sequences.

The cDNA of erythritol producing microorganism can be obtained by extracting RNA from the culture liquid of erythritol producing microorganism, preparing mRNA therefrom and carrying out reverse transcription reaction using the mRNA as a template.

For the extraction of RNA, it is convenient to use of TRIZOL (produced by Gibco BRL). Also, mRNA can be prepared conveniently by using DYNABEADS mRNA Purification Kit (produced by DYNAL).

Using the thus-obtained single strand cDNA as a template and the sense primer (cf. SEQ. ID No. 7 in the Sequence Listing) and antisense primer (cf. SEQ. ID No. 8 in the Sequence Listing) designed in advance, a probe was amplified by PCR reaction. In this manner, the present inventors succeeded in obtaining a cDNA fragment having a length of 398 bp as a PCR product.

The PCR product was ligated into a plasmid vector for transformation into *Esherichia coli* cells. Plasmids from transformant were analyzed by DNA sequencing using Dye Terminator and ABI 310A DNA sequencer (Perkin Elmer) for examining partial amino acid sequence of erythrose reductase type III.

As a result, it was confirmed that PCR product encodes a part of the erythrose reductase type III. The PCR product was used as a probe for the plaque hybridization as described below.

The fragment corresponds to the 184th to 582nd bases from the N-terminal of the base sequence described in SEQ. ID No. 1 of the Sequence Listing.

Subsequently, upon preparing the cDNA library of the erythritol producing microorganism, the present inventors studied in advance the time at which erythrose reductase type III mRNA highly expressed.

The method for examining the amount of expression of erythrose reductase type III includes Northern hybridization and the like methods. For example, total RNA was extracted from *Trichosporonoides megachiliensis* Strain SN-G42 cultivated for a varied time and Northern hybridization was carried out using the previously designed probe. As a result, it revealed that 48 hours cultivation product (Lane 3 in FIG. 2) showed the highest mRNA expression level for erythrose reductase type III.

Accordingly, the present inventors prepared a cDNA library of erythritol producing microorganism at the time when erythrose reductase type III mRNA highest expressed.

A cDNA library may be prepared by extracting RNA from a culture of erythritol producing microorganism, purifying mRNA, synthesizing double strand cDNA complementary thereto, and incorporating this into a phage vector with an adapter.

For the extraction of RNA, it is convenient to use TRIZOL (produced by Gibco BRL). Also, mRNA can be prepared conveniently by using DYNABEADS mRNA Purification Kit (produced by DYNAL).

The cDNA library can be prepared by adopting Okayama-Burg method, Gubler-Hoffman method or the like. However, for the convenience's sake, the latter method is preferred.

In practice, it is preferable and convenient to use the method of preparing a library using ZAP Express cDNA Synthesis Kit (produced by STRATAGENE) according to the manufacture instruction.

ZAP Express Vector used in the kit of the invention is a linear phage DNA. However, this can be taken out by in vivo excision as a circular plasmid (phagemid) containing kanamycin-resistant gene.

The present inventors performed screening of the above-described cDNA library for DNA encoding erythrose reductase type III using the previously obtained probe.

In the screening, the plaque hybridization was done using a probe labeled with digoxigenin.

The present inventors decoded the DNA sequence after converting a phage which is positive to the probe as a result of screening to a plasmid.

For example, first, several plaques that were positive to the probe in screening were isolated and phage was amplified. Then, a phagemid portion containing an insert was cleaved in viva from the phage DNA. This was converted into the form of plasmid in order to make the handling easy and transfected to *Escherichia coli* to amplify the plasmid. Thereafter, DNA sequencing was performed on this plasmid.

The present inventors have found a base sequence of a total length of 1,119 bp shown in SEQ. ID No. 1 in the Sequence Listing by the DNA sequencing.

The amino acid sequence determined based on this base sequence is also shown in SEQ. ID No. 2 in the Sequence Listing. The above amino acid sequence contains a partially decoded amino acid sequence, and the protein having this amino acid sequence was the erythrose reductase type III protein.

Figure 3:
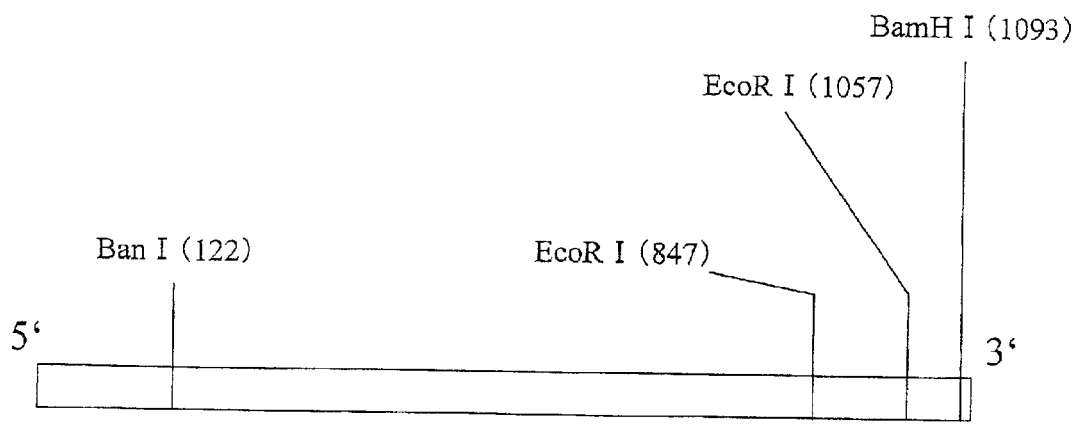
FIG. 3 is a restriction enzyme map of DNA encoding an erythrose reductase type III protein, wherein EcoR I, Ban I, and BamH I represent restriction enzymes, respectively and the numeral in the brackets indicates the number of bases counted from 5' terminal.

FIG. 3 shows a restriction enzyme map of the base sequence of DNA encoding erythrose reductase type III protein. As can be seen from FIG. 3, the base sequence has a Ban I cleavage site at the 122nd base from the 5'-terminal, EcoR I cleavage sites at 847th and 1057th bases from the 5'-terminal, and a BamH I cleavage site at the 1093rd base.

The amino acid sequence of the erythrose reductase type III protein (cf. SEQ. ID No. 2 of the Sequence Listing) is a novel amino acid having low homology with the previously clarified amino acid sequences of human aldose reductase and of yeast (*Saceharomyces cerevisiae*) gcy protein.

From this, it revealed that the erythrose reductase type III protein of the present invention had a novel amino acid sequence.

Next, the DNA of a protein having erythrose reductase activity of the second aspect of the present invention is illustrated.

The protein having said erythrose reductase activity of the present invention can be obtained by the following method.

That is, using a probe prepared based on full-length cDNA of the erythrose reductase type III of the above-described microorganism, screening of the cDNA library of the microorganism having an ability of producing erythrose is performed under the conditions described in item (b) of claim 3 and in claim 4, or in item (d) of claim 5 and in claim 6, whereby the protein having erythrose reductase activity of the second aspect of the present invention can be obtained.

The present inventors have found a base sequence of a total length of 1,077 bp shown in SEQ. ID No. 3 in the Sequence Listing as the DNA of a protein having erythrose reductase activity of the second aspect of the present invention.

The amino acid sequence determined based on this base sequence is also shown in SEQ. ID No. 4 in the Sequence Listing. Since the above amino acid sequence is identical with the partially decoded amino acid sequence, the protein having this amino acid sequence was the erythrose reductase type II protein.

Figure 4:
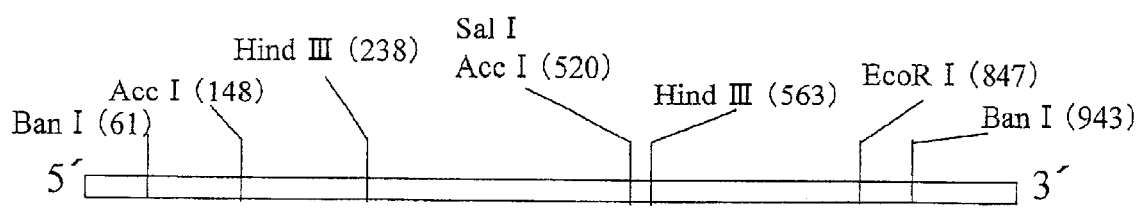
FIG. 4 is a restriction enzyme map of DNA encoding an erythrose reductase type II protein, wherein EcoR I, Ban I, Acc I, Hind III and Sal I represent restriction enzymes, respectively and the numeral in the brackets indicates the number of bases counted from 5' terminal.

FIG. 4 shows a restriction enzyme map of the base sequence of DNA encoding erythrose reductase type II protein. As can be seen from FIG. 4, the base sequence has Ban I cleavage sites on the 61st and 943rd base portions counted from the 5'-terminal, Acc I cleavage sites on the 148th and 520th base portions, Hind III cleavage sites on the 238th and 563rd base portions, an Sal I cleavage site on the 520th base portion, and an EcoR I cleavage site on the 847th base portion.

The amino acid sequence of the erythrose reductase type II protein (cf. SEQ. ID No. 4 of the Sequence Listing) is a novel amino acid sequence having low homology in comparison with the previously clarified amino acid sequences of human aldose reductase and of yeast gcy protein.

From this, it revealed that the erythrose reductase type II protein of the present invention had a novel amino acid sequence.

Hereinbelow, a method of obtaining the DNA of a protein having erythrose reductase activity of the third aspect of the present invention will be illustrated.

The protein having said erythrose reductase activity of the present invention can also be obtained by the same method as the above-described method for obtaining the protein having a erythrose reductase activity of the second aspect of the present invention.

That is, using a probe prepared based on full-length cDNA of the erythrose reductase type III of the above-described microorganism, screening of the cDNA library of the above-described microorganism is performed under the conditions described in item (b) of claim 3 and in claim 4, or in item (d) of claim 5 and in claim 6, whereby the protein having erythrose reductase activity of the third aspect of the present invention can be obtained.

The present inventors have found a base sequence of a total length of 1,121 bp shown in SEQ. ID No. 5 in the Sequence Listing as the DNA of a protein having erythrose reductase activity of the third aspect of the present invention.

The amino acid sequence determined based on this base sequence is also shown in SEQ. ID No. 6 in the Sequence Listing. Since the above amino acid sequence is identical with a partially decoded amino acid sequence, the protein having this amino acid sequence was the erythrose reductase type I protein.

Figure 5:
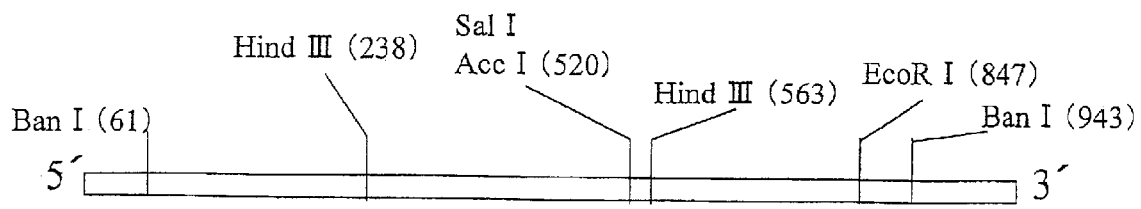
FIG. 5 is a restriction enzyme map of DNA encoding an erythrose reductase type I protein, wherein EcoR I, Ban I, Acc I, Hind III and Sal I represent restriction enzymes, respectively and the numeral in the brackets indicates the number of bases counted from 5' terminal.

FIG. 5 shows a restriction enzyme map of the base sequence of DNA encoding erythrose reductase type I protein. As can be seen from FIG. 5, the base sequence has Ban I cleavage sites on the 61st and 943rd base portions counted from the 5'-terminal, Hind III cleavage sites on the 238th and 563rd base portions, an Acc I cleavage site and an Sal I cleavage site on the 520th base portion, and an EcoR I cleavage site on the 847th base portion.

The amino acid sequence of the erythrose reductase type I protein (cf. SEQ. ID No. 6 of the Sequence Listing) is a novel amino acid sequence having low homology in comparison with the previously clarified amino acid sequences of human aldose reductase and of gcy protein.

From this, it revealed that the erythrose reductase type I protein of the present invention had a novel amino acid sequence.

The protein having an erythrose reductase activity according to the present invention may comprise an amino acid sequence containing one or more substitution, deletion, insertion, addition, or inversion at one or more sites with respect to the amino acid sequence of SEQ. ID No. 2, 4 or 6 in the Sequence Listing, if erythrose reductase activity exists.

The protein that comprises the amino acid sequence containing one or more substitution, deletion, insertion, addition or inversion at one or more sites with respect to the amino acid sequence of SEQ. ID No. 2, 4 or 6 in the Sequence Listing as such can be obtained, for example, by site specific mutation method (Methods in Enzymology, 100, pp. 448 (1983)), mutation treatment and in addition natural occurring mutation such as a difference in species or strain of an organism, and the like. Also, they can be obtained by manuals of experiments on genetic recombination (Nucleic Acid Res. 10, pp. 6487 (1982), Methods in Enzymol. 00, pp. 448 (1983)), PCR method (Molecular Cloning 2$^{nd}$ Edt., Cold Spring Harbor Laboratory Press (1989); PCR A Practical Approach IRL Press pp. 200 (1991)).

It can be confirmed by expressing the gene containing the sequence in a suitable cell and examining the erythrose reductase activity of the expression product whether said amino acid sequences containing the above-described substitution or the like have an erythrose reductase activity. The erythrose reductase activity can be measured by comparing changes in the amount of NAD(P)H since the enzyme uses NAD(P)H as a coenzyme upon reducing erythrose (cf. FIG. 1).

The DNA encoding the protein having an erythrose reductase activity of the first aspect of the present invention may be not only DNA containing the base sequence of base Nos. 1 to 399, which is, out of the base sequence described in SEQ. ID No. 1 in the Sequence Listing, on the N-terminal domain where it is predicted that the NAD(P)H binding site is mainly located but also DNA that hybridizes with a probe prepared from the above base sequence under stringent conditions and encodes a protein having an erythrose reductase activity.

Also, the DNA may be not only DNA containing the base sequence of base Nos. 408 to 1119, which is, out of the base sequence described in SEQ. ID No. 1 in the Sequence Listing, a portion on the C-terminal where the erythrose or erythritol binding site may be present but also DNA that hybridizes with a probe prepared from the above base sequence under stringent conditions and encodes a protein having an erythrose reductase activity.

The "stringent condition" referred to herein means the condition where a so-called specific hybrid forms without non-specific hybrid.

While this condition is difficult to be described in numerical values, mention may be made, for example, the condition under which hybridization is performed at a salt concentration corresponding to 2×SSC containing 0.1% SDS at 60° C., i.e., the condition of washing in usual Southern hybridization.

Among the DNA that hybridize under these conditions, those in which stop codon has been generated in the midway and those that have lost activity due to the variation in the active center may be included. They can be easily removed by ligating them to a commercially available expression vector, expressing them in a suitable host and measuring the erythrose reductase activity of the expressed product by the method described hereinbelow.

The DNA encoding the protein having an erythrose reductase activity of the second aspect of the present invention may be not only DNA containing the base sequence of base Nos. 1 to 399, which is, out of the base sequence described in SEQ. ID No. 3 in the Sequence Listing, on the N-terminal domain where it is predicted that the NAD(P)H binding site is mainly located but also DNA that hybridizes with a probe prepared from the above base sequence under stringent conditions and encodes a protein having an erythrose reductase activity.

Also, the DNA may be not only DNA containing the base sequence of base Nos. 408 to 1077, which is, out of the base sequence described in SEQ. ID No. 3 in the Sequence Listing, a portion on the C-terminal where the erythrose or erythritol binding site may be present but also DNA that hybridizes with a probe prepared from the above base sequence under stringent conditions and encodes a protein having an erythrose reductase activity.

The "stringent condition" referred to herein is also difficult to be described in numerical values, mention may be made, for example, the condition under which hybridization is performed at 60° C. and 2×SSC containing 0.1% SDS, i.e., the condition of washing in usual Southern hybridization.

The DNA encoding the protein having an erythrose reductase activity of the third aspect of the present invention may be not only DNA containing the base sequence of base Nos. 1 to 399, which is, out of the base sequence described in SEQ. ID No. 5 in the Sequence Listing, on the N-terminal domain where it is predicted that the NAD (P) H binding site is mainly located but also DNA that hybridizes with a probe prepared from the above base sequence under stringent conditions and encodes a protein having an erythrose reductase activity.

Also, the DNA may be not only DNA containing the base sequence of base Nos. 408 to 1121, which is, out of the base sequence described in SEQ. ID No. 5 in the Sequence Listing, a portion on the C-terminal where the erythrose or erythritol binding site may be present but also DNA that hybridizes with a probe prepared from the above base from 35% to 20 s to recover the fractions having erythrose reductase activity.

The "stringent condition" referred to is also difficult to be described in numerical values, mention may be made, for example, the condition under which hybridization is performed at 60° C. and 2×SSC containing 0.1% SDS, i.e., the condition of washing in usual Southern hybridization.

The DNA encoding the erythrose reductase type I, II or III activity protein can be introduced into a cell in the form in which the erythrose reductase expresses type I, II or III activity, respectively.

The introduction into a cell can be performed by amplifying by PCR the full length of DNA encoding the erythrose reductase type I, II or III with a primer having a restriction enzyme recognition site at both ends and ligation the amplified DNA into various expression vectors at the restriction enzyme site.

The cells, such as *Escherichia coli*, yeast (*Saccharomyces cerevisiae* and *Pichia pastoris*) and the like can be used for erythrose reductase expression.

As the plasmid, it is desirable to select suitable expression vectors for large scale production. In the case of *Escherichia coli*, plasmids encoding histidine tag-fused protein, GST (Glutathione-S-transferase)-fused protein, thioredoxin-fused protein and the like can be used.

Upon the induction of expression, a promoter may be incorporated upstream of the 5' side and a terminator may be incorporated downstream of the 3' side of the DNA of the present invention. As the promoter and terminator, those that are known to have a function in the cell for expression must be used. Details thereof are described in Biseibutsugaku Kisokoza 8, Idenshikogaku, Kyoritsu Shuppan (Fundamental Course on Microbiology 8, Genetic Engineering, Kyoritsu Publishing Co.), Adv. Biochem. Eng. 43, 75–102 (1990), Yeast 8, 423–488 (1992) and the like.

For example, where a plasmid is introduced into *Escherichia coli*, use of a regulation system by IPTG (isopropyl thiogalactopyranosid) at lactose operon and Lac I is preferable for tightly regulated induction.

Tightly regulated induction can be achieved by the use of galactose, when *Sacharomyces cerevisiae*, which is an auxotrophic yeast, is used in place of *E. coli*, and the plasmid is introduced into said yeast.

As described above, the protein having an erythrose reductase activity of the present invention can be produced by culturing cells to which DNA encoding a protein having an erythrose reductase activity is introduced, performing induction, harvesting the cells at a stage when the protein sufficiently expresses, separating recombinant proteins and purifying them.

Taking an example, a recombinant erythrose reductase type III can be produced by harvesting the cells to which DNA encoding the protein of the first aspect of the present invention by centrifugation, crushing the cells by ultrasonication, purifying the obtained recombinant proteins by affinity gel chromatography with histidine tag, and cleaving the histidine-tag off with enterokinase.

Similarly, recombinant erythrose reductase type II or I can be produced from cells into which DNA encoding a protein having an erythrose reductase activity of the second or third aspect of the present invention has been introduced.

The erythrose reductase activity can be monitored by measuring absorbance change at 340 nm in accordance with NADPH or NADH consumption upon reducing D-erythrose (cf. FIG. 1).

Next, the method for producing erythritol with the present invention will be described. Specifically, meso-erythritol can be obtained by making the protein of the present invention act on D-erythrose.

Upon making the protein having erythrose reductase activity of the present invention to act on D-erythrose, a reduction reaction of the D-erythrose can be done in the presence of NADPH or NADH, at an optional condition for expressing the enzyme activity.

The reduction reaction can be performed at a reaction temperature of 33 to 37° C., preferably 36 to 37° C., pH 6.0 to 7.0, preferably pH 6.5, in a coenzyme NADPH or NADH concentration of 0.1 to 0.5 mM, preferably 0.2 to 0.3 mM. The substrates can be added at the starting point for the reaction but it is desirable to continuously or non-continuously add the substrate so that the concentration of substrate in the reaction mixture will not become too high.

Also, erythritol can be obtained by making the cell to which the DNA encoding an erythrose reductase protein has been introduced to act on D-erythrose. In this case, erythrose reductase protein reduces D-erythrose, using intercellular NADPH or NADH. That is to say, it needs not to add NAD(P)H exteriorly.

Taking an example, erythritol can be obtained by culturing the cells to which the DNA encoding erythrose reductase protein is incorporated under a suitable condition for the growth of the cells and the production of erythritol in a medium containing properly a carbon source selected from sugars such as glucose, fructose, sucrose and the like, a nitrogen source selected from yeast extracts, peptone and the like, and an inorganic salts selected from phosphoric acid salts, magnesium salts, calcium salts, etc.

The recombinant erythrose reductases type I, II and III of the present invention has a substrate specificity equivalent to that of the erythrose reductases reported and has an enzymatic activity of producing sugar alcohol.

According to the present invention, a novel protein having an erythrose reductase activity can be provided.

Expression of DNA encoding the erythrose reductases type III, II or I of the present invention, for example, microorganisms including yeast make it easy to perform large scale production of erythrose reductases type III, II or I independently of the productivity of the microorganisms and the like as compared with the known methods by normally culturing microorganisms.

The recombinant erythrose reductases type III, II or I have equivalent substrate specificity to that of natural type erythrose reductases and also retain an enzymatic activity of producing sugar alchols.

Therefore, the erythrose reductases type III, II or I produced by utilizing DNA encoding the enzyme of the present invention are useful in the production of erythritol on an industrial scale.

Moreover, DNA encoding the erythrose reductases type III, II or I of the present invention is also useful in various applications such as development of mutant enzymes having high erythritol productivity by genetic engineering techniques and cloning of genes encoding related enzymes.

EXAMPLES

Hereinafter, the present invention will be explained in detail with examples. However, the present invention should not be construed as being limited thereto.

Example 1

(1) Harvesting and Purification of Erythrose Reductase Type III from *Trichosporonoides megachiliensis* Strain SN-G42

Following the method described in H. Ishizuka, et al., Biosci. Biotech. Biochem., 56(6), 941-945, 1992, harvesting and purification of erythrose reductases type III from *Trichosporonoides megachiliensis* strain SN-G42 (FERM BP-1430, under the old name of Aureobasidium strain SN-G42; this strain is deposited under the Budapest Treaty on the National Institute of Bioscience and Human Technology (NIBH), Agency of Industrial Science and Technology, Ministry of International Trade and Industry) was performed.

First, *Trichosporonoides megachiliensis* Strain SN-G42 (FERM BP-1430) was cultured for 72 hours in glucose medium (40% glucose, 2% yeast extracts, 2 liters).

The cells were collected by centrifugation at 10,000×g for 30 minutes then freeze-dried, treated with acetone, and thereafter homogenized using MSK Cell homogenizer (produced by B. Braun Japan).

Next, the crushed cells were centrifuged at 10,000×g for 30 minutes in 4° C. to remove cell debris.

The supernatant was subsequently fractionated by ammonium sulfate precipitation. The precipitants between 40 to 70% ammonium sulfate including erythrose reductase were condensed by membrane filtration. Then, the precipitants were dissolved into 50 mM glycine-NaOH buffer (pH 9.0). After removing insoluble materials by centrifugation, the enzyme fraction was dialyzed against the above-described buffer solution at 4° C. for 24 hours.

The dialyzed sample was loaded on a column of DEAE-Toyopearl 650S (1.4×20 cm) (produced by Tosoh Corp.) previously equilibrated with 50 mM glycine-NaOH buffer solution (pH 9.0) and the concentration of sodium chloride was linearly increased from 0 mM to 100 mM, followed by recovering the fractions containing erythrose reductase activity.

The active fractions were condensed by ammonium sulfate precipitation and loaded on a column of AF-Blue Toyopearl 650 ML (1.4×20 cm) (produced by Tosoh Corp.) previously equilibrated with 10 mM phosphate buffer solution (pH 6.0) and the concentration of sodium chloride was increased stepwise from 0 mM to 200 mM, followed by separating the fractions containing erythrose reductases type I and type II (non-adsorbed fractions) and fractions containing erythrose reductase type III (adsorbed fractions).

After collecting and condensing them, the fractions containing erythrose reductase type III were loaded on a column of Butyl-Toyopearl 650S (11×20 cm) (produced by Tosoh Corp.), a column for hydrophobic chromatography previously equilibrated with 35% saturated ammonium sulfate-10 mM phosphate buffer solution (pH 6.0), and 10 mM phosphate buffer solution (pH 6.0) was passed under a gradient of concentration of ammonium sulfate linearly descending from 35% to 20% to recover the fractions having erythrose reductase activity.

Thus, erythrose reductase type III was purified.

(2) Determination of a Partial Amino Acid Sequence of Erythrose Reductase Type III Peptide mapping of the above-purified erythrose reductase type III was performed to determine a partial amino acid sequence.

The erythrose reductase type III was pyridylethylated (H. Hirano: J. Protein Chem., 8, 115 (1989)) and digested with lysyl endopeptidase (produced by Roche). Separation of this sample using ODS-80 Tm (produced by Tosoh Corp.) column showed 14 peaks, two of which were determined for amino acid sequence using Peptide Sequencer 477A (produced by Perkin-Elmer).

(3) Design of a Primer Used in PCR Reaction

Of the partially decoded amino acid sequence, those amino acid sequences (cf. SEQ. ID Nos. 9 and 10 in the Sequence Listing) selected with reference to the amino acid sequences in among aldo-keto reductase family were used as a sense primer (cf. SEQ. ID No. 7 in the Sequence Listing) and an antisense primer (cf. SEQ. ID No. 8 in the Sequence Listing) in the PCR reaction described hereinbelow.

(4) PCR of cDNA Fragment Encoding Erythrose Reductase Type III

Next, to prepare a probe for use in the screening and the like as described below, PCR was performed.

Single strand cDNA was synthesized from *Trichosporonoides megachiliensis* strain SN-G42 cultured for 3 days in 40% glucose medium by the following procedures and used as a template.

RNA was extracted from the culture cell using TRIZOL (produced by Gibco BRL) and mRNA was purified using a DYNABEADS mRNA Purification Kit (produced by DYNAL).

Reverse transcription reaction was carried out using the purified mRNA as a template to synthesize cDNA.

In the reaction, Super Script™ Reverse Transcriptase (produced by Gibco) was used as a reverse transcriptase and Oligo (dT)$_{12-15}$ primer (produced by Amersham Pharmacia Biotech) as a primer.

The composition of the reverse transcription reaction mixture was as follows:

| mRNA | 1 µg |
|---|---|
| dNTP | 10 mM × 3 µL |
| Primer | 0.5 µg |

RNA transcription was carried out at 42° C. for 1 hour.

Using the thus-obtained cDNA as a template, the sense primer (cf. SEQ. ID No. 7 in the Sequence Listing) and antisense primer (cf. SEQ. ID No. 8 in the Sequence Listing) for PCR designed in (3) above, and Pfu DNA polymerase (produced by STRATAGENE), PCR reaction was carried out 25 cycles, each cycle being 94° C., 1 minute—40° C., 1 minute—72° C., 1 minute.

The amplification product of PCR reaction was a cDNA fragment of a length of 398 bp. The fragment was ligated to a vector pBS SK+ digested with EcoR V and further was transformed with DH5α strain. Whether or not the transformant contained the partial amino acid sequence of the previously determined erythrose reductase type III protein was analyzed.

The cDNA fragment obtained was consequently identified as being a partial cDNA of erythrose reductase type III. This fragment corresponded to 184th to 582nd from the N-terminal of the base sequence described in SEQ. ID No. 1 in the Sequence Listing.

This cDNA fragment was used as a probe for the further cDNA isolation.

(5) Northern Hybridization of *Trichosporonoides megachiliensis* Strain SN-G42

Upon preparing cDNA library of *Trichosporonoides megachiliensis* strain SN-G42, Northern hybridization was performed in order to study when the microorganism express mRNA for erythrose reductase type III.

*Trichosporonoides megachiliensis* strain SN-G42 was cultured with shaking under the condition of 37° C. and 220 rpm in a 500 ml flask using 30 ml of a medium containing 40% glucose for 24, 48, 72 or 96 hours.

After the culture, total RNA was extracted from each cells using TRIZOL (produced by Gibco BRL).

The probe prepared from the previously decoded purified enzyme was used after labeling with digoxigenin-UTP using DIG RNA Labeling kit (produced by Roche).

Extracted RNAs was electrophoresed, then blotted onto a Hybond-N membrane. Northern hybridization was carried out with the above RNA-labeled probe under high stringent condition.

Figure 2:
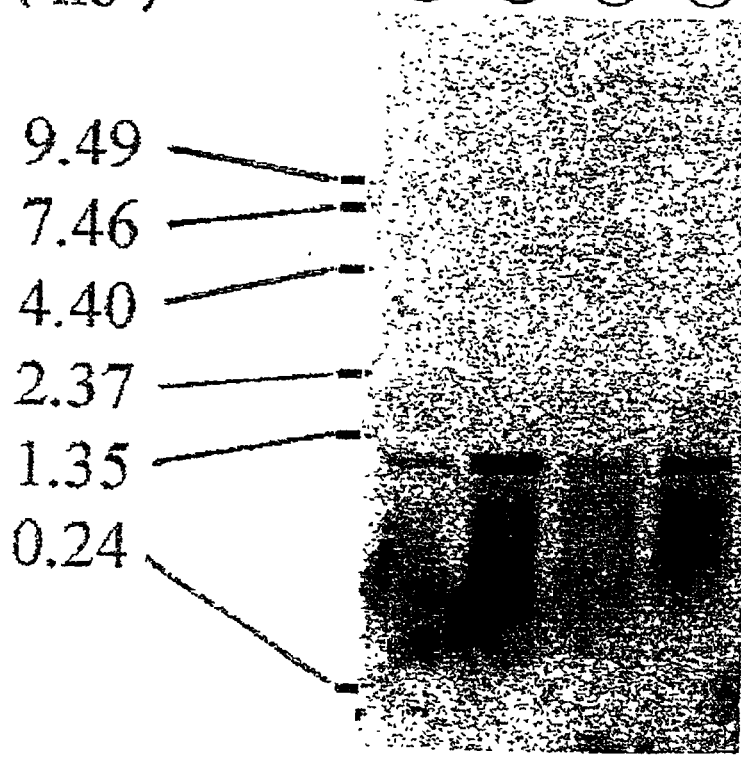
FIG. 2 is an electrophoretogram showing the results of Northern hybridization, wherein Lane 1 shows the result on the product of 24 hours cultivation, Lane 2 shows the result on the product of 48 hours cultivation, Lane 3 shows the result on the product of 72 hours cultivation, and Lane 4 shows the result of the product of 96 hours cultivation.

FIG. 2 shows the results of Northern hybridization. In FIG. 2, Lane 1 shows the results on the product of 24 hours culture, Lane 2; 48 hours, Lane 3; 72 hours and Lane 4; 96 hours. In order to compare the lengths of fragments, the mobility of RNA Ladder was marked on the left side.

From FIG. 2, it was found that the band of around 1.0 kb was strongest at 48 hour culture, and that the erythrose reductase type III was expressed.

From these results, it is clear that the 48 hour culture of *Trichosporonoides megachiliensis* strain SN-G42 expressed erythrose reductase type III highest. This reveals that the cDNA library prepared from mRNA at this time is suitable for gene analysis of the above-described enzyme.

(6) Preparation of cDNA Library of *Trichosporonoides megachiliensis* Strain SN-G42

In accordance with the results in (5) above, a cDNA library was prepared from mRNA at the time when erythrose reductase type III expressed highest by the following procedure.

*Trichosporonoides megachiliensis* strain SN-G42 was cultivated in 30 ml of a medium containing 40% glucose in a 500 ml flask under the conditions of 37° C., 220 rpm and 48 hours.

RNA was extracted from the culture using TRIZOL (produced by Gibco BRL) and mRNA was purified using DYNABEADS mRNA Purification Kit (produced by DYNAL).

From the mRNA, a library was prepared using ZAP Express cDNA Synthesis Kit (produced by STRATAGENE) with the description of the kit. First, reverse transcription reaction was carried out using mRNA as a template to synthesize cDNA.

On this occasion, Moloney murine leukemia virus reverse transcriptase (MMLV-RT, produced by STRATAGENE) was used as a reverse transcriptase and linker primer was used as a primer. These are reagents contained in the above-described kit.

The composition of reverse transcription reaction mixture was as follows.

| | |
|---|---|
| mRNA | 5 μg |
| dNTP | 10 mM × 3 μL |
| Primer | 2.8 μg |

The obtained cDNA was inserted into ZAP Express Vector utilizing EcoR I site and Xho I site to package it.

In this manner, the cDNA library of *Trichosporonoides megachiliensis* strain SN-G42 having a titer of 2,350,000 pfu was prepared.

(7) Plaque Hybridization of cDNA Library and Determination of Base Sequence of DNA Encoding an Erythrose Reductase Type III Protein Next, packaged recombinant phage was infected to *Escherichia coli* XL1-Blue MRF' and was allowed to form plaques on the plate. Then, using the probe prepared in (4) above, plaque hybridization was carried out under the stringent conditions.

As a result of the plaque hybridization, the target clone was isolated and amplified and thereafter by acting helperphage, only the phagemid portion in the λ-phage DNA (including an insert) was cleaved and cyclized to form a plasmid. This was infected to host *Escherichia coli* XLOLR and amplified therein.

Then, a plasmid was obtained from the amplified XLOLR and DNA sequencing was performed.

As a result of analyses, this revealed to be a base sequence described in SEQ. ID No. 1 in the Sequence Listing of a full length of 1,119 bp. The translation of the base sequence into amino acid was also shown in SEQ. ID No. 2 in the Sequence Listing.

Furthermore, a restriction enzyme map on the obtained base sequence was prepared by the conventional manner (FIG. 3). As will be apparent from FIG. 3, the base sequence has a Ban I cleavage site on the 122nd base portion counted from the 5'-terminal, EcoR I cleavage sites in the 847th and 1057th base portions and BamH I cleavage site on the 1093rd base portion.

The erythrose reductase type III protein consisting of the amino acid sequence described in SEQ. ID No. 2 in the Sequence Listing revealed to be a novel sequence having low homology with the known amino acid sequences such as the previously elucidated human aldose reductase enzyme and yeast gcy protein.

From this it revealed that the DNA encoding the erythrose reductase type III protein of the present invention has the sequence described in SEQ. ID No. 1 so that the erythrose reductase type III of the present invention revealed to be a DNA encoding a polypeptide having a novel amino acid sequence.

(8) Expression of Recombinant Erythrose Reductase Type III Using *Escherichia coli*

Based on the N-terminal side of the base sequence described in SEQ. ID No. 1 in the Sequence Listing except the initiation-codon (atg), a primer was prepared so as to have a BamH I site. Also, based on the C-terminal side of the same base sequence, another primer was synthesized so as to have an Xho I site.

Using as a template a plasmid containing erythrose reductase type III, which had been obtained by previously performing screening from the cDNA library, full-length cDNA of erythrose reductase type III having BamH I and Xho I sites on the terminals was amplified by PCR using the above-described primers.

The conditions of PCR were such that 200 ng of plasmid containing erythrose reductase type III cDNA was used as a template and Pfu DNA polymerase (produced by STRATAGENE) was used as an enzyme and PCR was carried out at 12 cycles.

As a result of PCR, erythrose reductase type III gene having BamH I and Xho I sites was amplified. The PCR amplification product was incorporated by cleaving the BamH I and Xho I sites of plasmid pRSET A (produced by INVITROGEN).

The plasmid pRSET A in a state having incorporated therein erythrose reductase type III gene was introduced into *E. coli* BL21 (DE3) pLysS (prepared by STRATAGENE), which is a cell for expression, and *E. coli* was cultivated on an LB culture medium containing 50 μg/mL of Ampicillin at 25° C. so that it could be expressed as histidine Tag bonded protein. The induction of expression was performed through lactose operon by adding IPTG so as to be at a final concentration of 1 mM.

Cells of *E. coli* were collected by centrifugation (2,920×g, 15 minutes) and crushed by sonication treatment (SONIFIER 250D, produced by BRANSON), and centrifugation (26,400×g, 15 minutes) was performed again to obtain supernatant (crude enzyme solution).

The obtained crude enzyme solution was purified through Nickel Chelated Agarose (B-PER 6×His Spin Purification Kit, produced by PIERCE), which is an affinity gel for a histidine Tag-fused protein.

Next, using a gel filtration unit PD-10 (produced by Amersham Pharmacia Biotech), the buffer was replaced with an enterokinase reaction buffer using gel filtration.

After the purification, the histidine Tag portion was cleaved with enterokinase (produced by INVITROGEN). Thereafter, to remove contaminant proteins, histidine Tag, and enterokinase, purification by ion exchange column was performed to obtain recombinant erythrose reductase type III.

Example 2

(1) Plaque Hybridization of cDNA Library and Determination of Base Sequence of DNA Encoding an Erythrose Reductase Type II Protein On the cDNA library prepared in Example 1 (6), a probe was prepared based on full-length cDNA of erythrose reductase type III obtained in Example 1 above, and plaque hybridization was carried out using this probe under the stringent conditions.

As a result of the plaque hybridization, the target clone was isolated and amplified, and thereafter, by acting helperphage only the phagemid portion in the λ-phage DNA (including an insert) was cleaved and cyclized to form a plasmid. This plasmid was infected to host *E. coli* XLOLR and amplified therein.

Then, a plasmid was obtained from the amplified XLOLR, and DNA sequencing was performed.

As a result of analyses, it was revealed that this is a base sequence described in SEQ. ID No. 3 in the Sequence Listing of a full length of 1,077 bp. The translation of the base sequence into amino acid was also shown in SEQ. ID No. 4 in the Sequence Listing.

Furthermore, a restriction enzyme map on the obtained base sequence was prepared by the conventional manner (FIG. 4). As can be seen from FIG. 4, the base sequence has Ban I cleavage sites on the 61st and 943rd base portions counted from the 5'-terminal, Acc I cleavage sites on the 148th and 520th base portions, Hind III cleavage sites on the 238th and 563rd base portions, an Sal I cleavage site on the 520th base portion, and an EcoR I cleavage site on the 847th base portion.

From this, it was revealed that the DNA encoding the erythrose reductase type II protein of the present invention has the sequence described in SEQ. ID No. 3 so that the erythrose reductase type II gene of the present invention revealed to be a DNA encoding a polypeptide having a novel amino acid sequence.

(2) Expression of Recombinant Erythrose Reductase Type II Using E. coli.

Based on the N-terminal side of the base sequence described in SEQ. ID No. 3 in the Sequence Listing except the initiation codon (atg), a primer was prepared so as to have a BamH I site. Also, based on the C-terminal side of the same base sequence, another primer was synthesized so as to have an Xho I site.

Using as a template a plasmid containing erythrose reductase type II, which had been obtained by previously performing screening from the cDNA library, full-length cDNA of erythrose reductase type II having BamH I and Xho I sites on the terminals was amplified by PCR using the above-described primers. The conditions of PCR were the same as shown in Example 1 (8).

As a result of PCR, erythrose reductase type II gene having BamH I and Xho I sites was amplified. The PCR amplification product was incorporated by cleaving the BamH I and Xho I sites of plasmid pRSET A and purified in the same manner as in Example 1 (8) to obtain recombinant erythrose reductase type II.

Example 3

(1) Plaque Hybridization of cDNA Library and Determination of Base Sequence of DNA Encoding an Erythrose Reductase Type I Protein On the cDNA library prepared in Example 1 (6), a probe was prepared based on full-length cDNA of erythrose reductase type III A obtained in Example 1 above, and plaque hybridization was carried out using this probe under the stringent conditions.

As a result of the plaque hybridization, the target clone was isolated and amplified, and thereafter, by acting helper-phage only the phagemid portion in the λ-phage DNA (including an insert) was cleaved and cyclized to form a plasmid. This plasmid was infected to host E. coli XLOLR and amplified therein.

Then, a plasmid was obtained from the amplified XLOLR, and DNA sequencing was performed.

As a results of analyses, it was revealed that this is a base sequence described in SEQ. ID No. 5 in the Sequence Listing of a full length of 1,121 bp. The translation of the base sequence into amino acid was also shown in SEQ. ID No. 6 in the Sequence Listing.

The present inventors have found a base sequence of a total length of 1,121 by shown in SEQ. ID No. 5 in the Sequence Listing by the DNA sequencing.

Furthermore, a restriction enzyme map on the obtained base sequence was prepared by the conventional manner (FIG. 5). As can be seen from FIG. 5, the base sequence has Ban I cleavage sites on the 61st and 943rd base portions counted from the 5'-terminal, Hind III cleavage sites on the 238th and 563rd base portions, an Acc I cleavage site and an Sal I cleavage site on the 520th base portion, and an EcoR I cleavage site on the 847th base portion.

From this, it was revealed that the DNA encoding the erythrose reductase type I protein of the present invention has the sequence described in SEQ. ID No. 5 and thus the erythrose reductase type I gene of the present invention revealed to be a DNA encoding a polypeptide having a novel amino acid sequence.

(2) Expression of Recombinant Erythrose Reductase Type I Using E. coli.

Based on the N-terminal side of the base sequence described in SEQ. ID No. 5 in the Sequence Listing except the initiation codon (atg), a primer was prepared so as to have a BamH I site. Also, based on the C-terminal side of the same base sequence, another primer was synthesized so as to have an Xho I site.

Using as a template a plasmid containing erythrose reductase type I, which had been obtained by previously performing screening from the cDNA library, full-length cDNA of erythrose reductase type I having BamH I and Xho I sites on the terminals was amplified by PCR using the above-described primers. The conditions of PCR were the same as those shown in Example 1 (8)

As a result of PCR, erythrose reductase type I gene having BamH I and Xho I sites was amplified. The PCR amplification product was incorporated by cleaving the BamH I and Xho I sites of plasmid pRSET A and purified in the same manner as in Example 1 (8) to obtain recombinant erythrose reductase type I.

Example 4

The following tests were carried out on the purified recombinant erythrose reductases type III, type II, and type I obtained in Examples 1 to 3.

(1) Comparison of Substrate Specificity

The substrate specificities of the purified recombinant erythrose reductases type III, type II, and type I were compared with that of the erythrose reductase heretofore reported (natural type: H. Ishizuka et al., Biosci. Biotech. Biochem., 56(6), 941–945, 1992).

In the presence of 50 mM of a phosphate buffer at pH 6.5, 12 mM of a substrate, and 0.2 mM of NADPH, 20 μL of an enzyme was acted (1 mL in total), and a change with time in optical absorbance at 340 nm was measured at 37° C. for 5 minutes.

With the reaction rate at which erythrose is reduced as a substrate as being 100%, relative values (%) of reaction rates for reducing various ketoses and aldoses are shown in Table 1.

TABLE 1

| | Relative value (%) | | | |
| --- | --- | --- | --- | --- |
| | Normal type | Recombinant type | | |
| Substrate | Type III | Type III | Type II | Type I |
| Dihydroxyacetone | 20.0 | 20.3 | 11.2 | 11.4 |
| D-glyceraldehyde | 66.0 | 98.2 | 107.8 | 102.0 |
| D-erythrose | 100.0 | 100.0 | 100.0 | 100.0 |
| L-erythrulose | 38.0 | N.D | N.D | N.D |
| D-ribose | 1.2 | 2.3 | 0.7 | 1.0 |
| D-arabinose | 0.0 | 0.0 | 0.0 | 0.9 |
| D-xylose | 1.2 | 4.5 | 2.4 | 3.2 |
| D-xylulose | 0.0 | 7.8 | 3.5 | 7.5 |
| D-glucose | 0.0 | 0.0 | 0.0 | 0.0 |
| D-mannose | 0.0 | 0.0 | 0.0 | 0.0 |
| D-galactose | 0.0 | 0.0 | 0.0 | 0.0 |
| D-fructose | 0.0 | 0.0 | 0.0 | 0.0 |
| L-sorbose | 0.0 | 0.0 | 0.0 | 0.0 |
| Trehalose | 0.0 | 0.0 | 0.0 | 0.0 |
| D-glucuronate | 6.6 | 0.8 | 0.0 | 0.7 |
| p-nitrobenzaldehyde | 46.0 | 66.3 | 8.8 | 11.5 |

From Table 1, it is clear that the purified recombinant erythrose reductase type III of the present invention has an ability of reducing substrates of heretofore reported natural type erythrose reductase type III.

Furthermore, the substrate specificities of the purified recombinant erythrose reductases type I and type II were characterized by having a lower relative activity on dihydroxyacetone and p-nitrobenzaldehyde than type III.

From the above, it is apparent that the recombinant enzyme obtained by the expression of DNA encoding the erythrose reductase type III of the present invention has the same substrate specificity as the naturally occurring erythrose reductase type III and has an enzyme activity of producing sugar alcohols.

Furthermore, it is also apparent that the recombinant enzymes obtained by the expression of DNA encoding the erythrose reductases type II and type I of the present invention have an enzyme activity of producing sugar alcohols such as erythritol.

(2) Western Blotting

Western Blotting was carried out on the purified recombinant erythrose reductases type III, type II, and type I.

The enzyme solution containing each enzyme was separated by SDS-PAGE, and transferred from the gel to a PVDF membrane after the separation. After this was reacted with an anti-erythrose reductase type III mouse antibody as the primary antibody, the primary antibody linking thereto was detected using a sheep anti-mouse IgG antibody labeled with HRP. The results are shown in FIG. 6.

Figure 6:
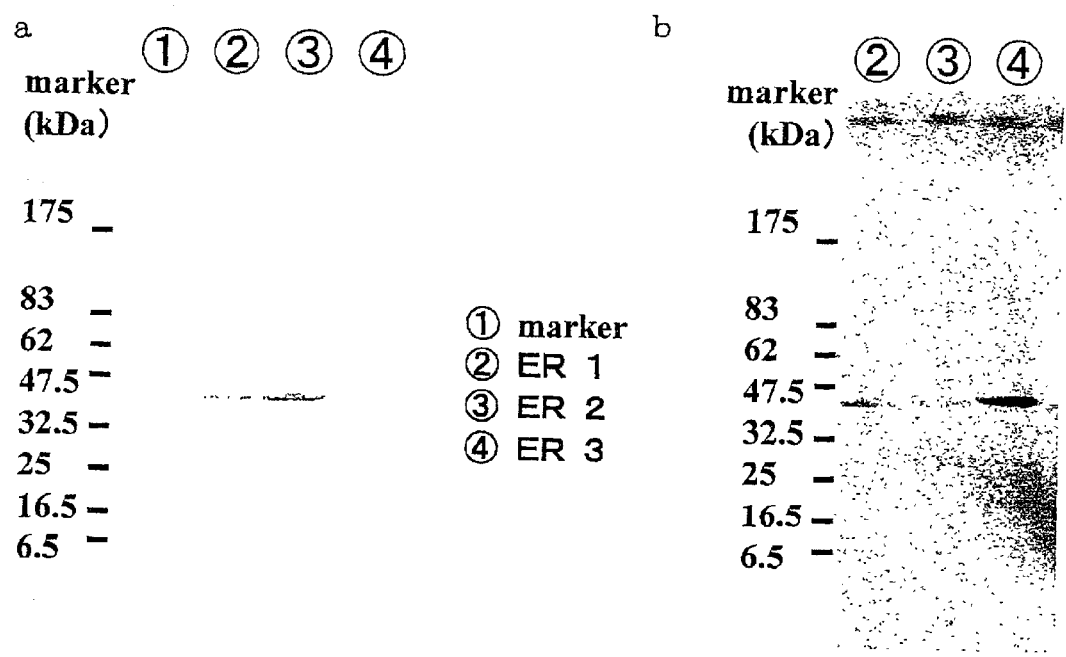
FIG. 6 is an electrophoretogram showing the results of Western blotting on erythrose reductase, wherein a shows the result of SDS-PAGE on the recombinant erythrose reductase, b shows the result of Western blotting performed by transferring the above SDS-PAGE pattern to a PVDF membrane. In a and b in FIG. 6, Lane 1 shows the molecular weight marker (kDa), Lane 2 shows the result on the purified recombinant erythrose reductase type I, Lane 3 shows the result on the purified recombinant erythrose reductase type II, and Lane 4 shows the result on the purified recombinant erythrose reductase type III.

In FIG. 6, a shows the result of SDS-PAGE on the purified recombinant erythrose reductase of the present Example, and b shows the result of Western blotting performed by transferring the above SDS-PAGE pattern to a PVDF membrane.

In a and b in FIG. 6, Lane 1 shows the molecular weight marker (kDa), Lane 2 shows the result on the purified recombinant erythrose reductase type I, Lane 3 shows the result on the purified recombinant erythrose reductase type II, and Lane 4 shows the result on the purified recombinant erythrose reductase type III.

As is apparent from FIG. 6, antibody reaction was clearly detected on the purified recombinant erythrose reductase type III.

On the purified recombinant erythrose reductases type I and type II, antibody reaction was also detected although its reactivity was low.

(3) SDS-PAGE

On the purified recombinant erythrose reductases type III, type II, and type I, SDS-PAGE was carried out with a fully automatic electrophoresis system called Phast System (produced by Amersham Pharmacia Biotech), using a gel (trade name: Phast Gel (Gradient 8–25), manufacturer: Amersham Pharmacia Biotech).

Figure 7:
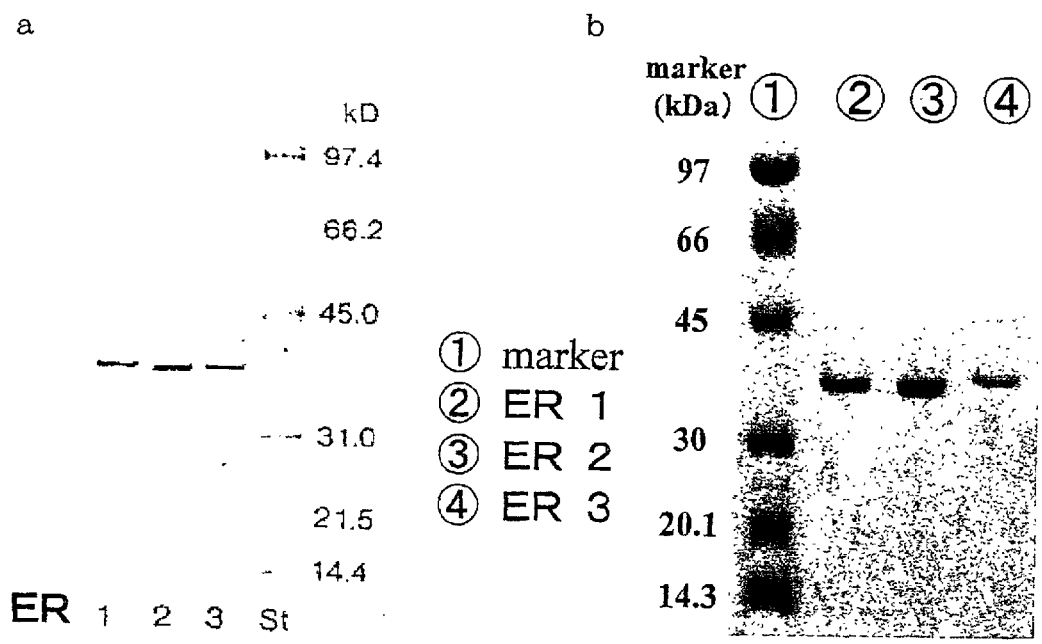
FIG. 7 is an electrophoretogram showing the results of SDS-PAGE on erythrose reductase, wherein a shows the result on natural type erythrose reductase, b shows the result on the recombinant erythrose reductase. ER 1, 2 and 3 in FIG. 7a show the results on the natural type erythrose reductase type I, II and III respectively, and in b, Lane 1 shows the molecular weight marker (kDa), Lane 2 shows the result on the purified recombinant erythrose reductase type I, Lane 3 shows the result on the purified recombinant erythrose reductase type II, and Lane 4 shows the result on the purified recombinant erythrose reductase type III.

The results are shown in FIG. 7.

In FIG. 7, a shows the result on the erythrose reductase heretofore reported (natural type: K. Tokuoka et al., J. Gen. Appl. Microbiol., 38, 145–155), and b shows the results on the purified recombinant erythrose reductases of the present invention.

In FIG. 7, ER 1, 2 and 3 in FIG. 7a show the results on the natural type erythrose reductase type I, II and III respectively, and in b, Lane 1 shows the molecular weight marker (kDa), Lane 2 shows the result on the purified recombinant erythrose reductase type I, Lane 3 shows the result on the purified recombinant erythrose reductase type II, and Lane 4 shows the result on the purified recombinant erythrose reductase type III.

As is apparent from FIG. 7b, for all of the purified recombinant erythrose reductases type I, type II, and type III, a band was confirmed at the portion of about 37 kDa (37,000 Da) that is anticipated from each amino acid sequence. This was the same result as that on natural type erythrose reductase (FIG. 7a)

(4) Native-PAGE

On the purified recombinant erythrose reductases type III, type II, and type I, Native-PAGE was carried out with a fully automatic electrophoresis system called Phast System (produced by Amersham Pharmacia Biotech), using a gel (trade name: Phast Gel (Gradient 8–25), manufacturer: Amersham Pharmacia Biotech). The results are shown in FIG. 8.

Figure 8:
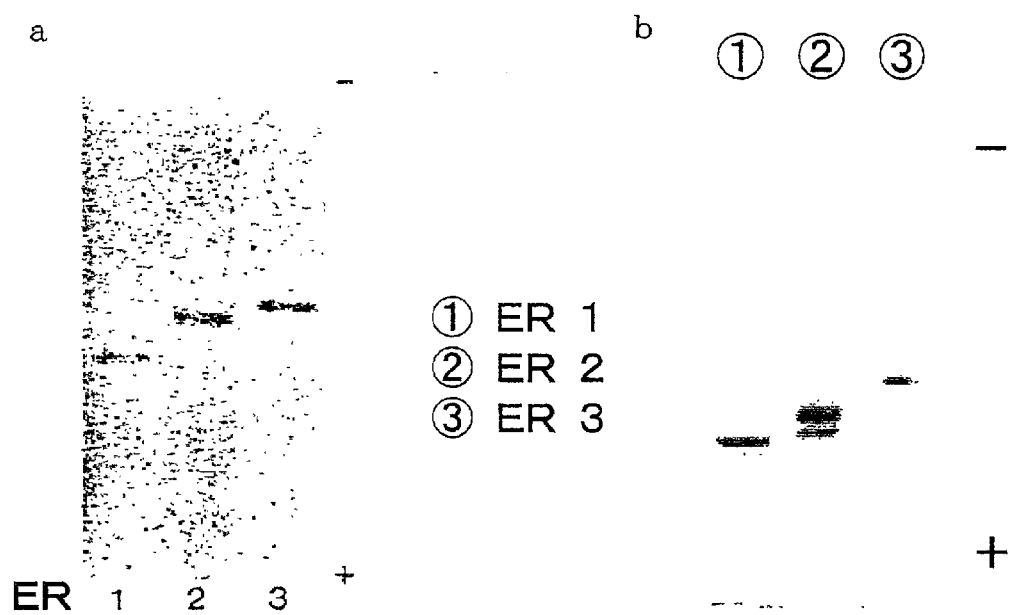
FIG. 8 is an electrophoretogram showing the results of Native-PAGE on erythrose reductase, wherein a shows the result on natural type erythrose reductase, b shows the result on the recombinant erythrose reductase. ER 1, 2 and 3 in FIG. 8a show the results on the natural type erythrose reductase type I, II and III respectively, and in b, Lane 1 shows the result on the purified recombinant erythrose reductase type I, Lane 2 shows the result on the purified recombinant erythrose reductase type II, and Lane 3 shows the result on the purified recombinant erythrose reductase type III.

In FIG. 8, a shows the result on the erythrose reductase heretofore reported (natural type: K. Tokuoka et al., J. Gen. Appl. Microbiol., 38, 145–155), and b shows the results on the purified recombinant erythrose reductases of the present invention.

In FIG. 8, ER 1, 2 and 3 in FIG. 8a show the results on the natural type erythrose reductase type I, II and III respectively, and in b, Lane 1 shows the result on the purified recombinant erythrose reductase type I, Lane 2 shows the result on the purified recombinant erythrose reductase type II, and Lane 3 shows the result on the purified recombinant erythrose reductase type III.

From FIG. 8b, referring to the results, the pattern of relative mobility of each recombinant enzyme was almost the same as the data obtained on natural type erythrose reductase (FIG. 8a).

Incidentally, in the purified recombinant erythrose reductases type I and type II, two bands are observed. It is considered that the non-main band corresponds to an enzyme in which histidine Tag was not completely cleaved in purification.

(5) IEF-PAGE (Isoelectric Focusing)

On the purified recombinant erythrose reductases, IEF-PAGE was carried out with a fully automatic electrophoresis system called Phast System (produced by Amersham Pharmacia Biotech), using a gel (trade name: Phast Gel (IEF pH 4–6.5), manufacturer: Amersham Pharmacia Biotech).

Electrophoresis was conducted using a pH gradient gel, and the separated proteins were stained.

Figure 9:
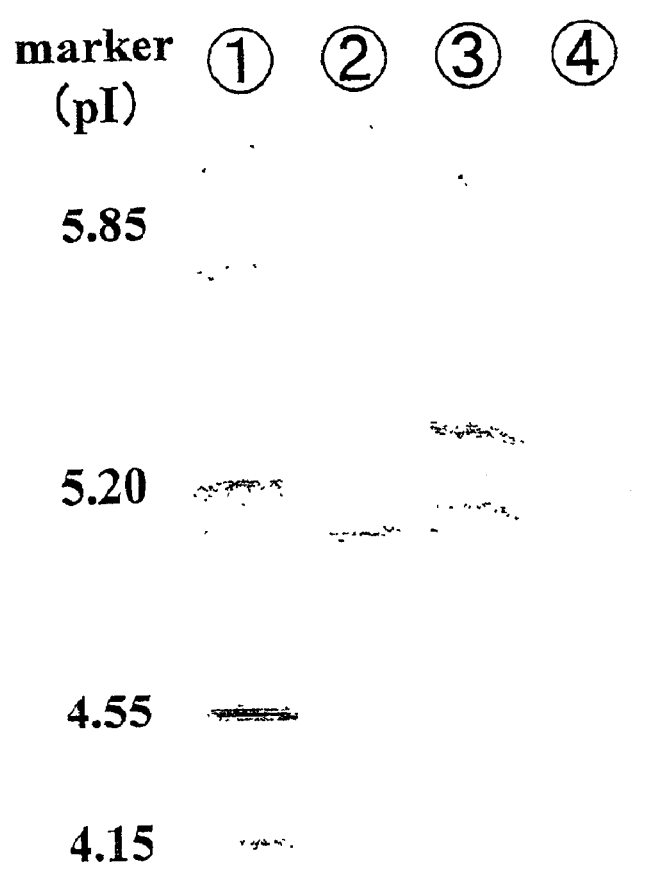

The results are shown in FIG. 9.

In FIG. 9, Lane 1 shows the isoelectric point marker protein, Lane 2 shows the result on the purified recombinant erythrose reductase type I, Lane 3 shows the result on the purified recombinant erythrose reductase type II, and Lane 4 shows the result on the purified recombinant erythrose reductase type III.

From FIG. 9, the isoelectric point of each enzyme could be confirmed from the mobility of a band. That is, the purified recombinant erythrose reductase type I had a pI of 4.7, the purified recombinant erythrose reductase type II had a pI of 5.3, and the purified recombinant erythrose reductase type III had a pI of 5.8.

Incidentally, in the purified recombinant erythrose reductases type I and type II, two bands are observed. It is considered that the non-main band corresponds to an enzyme in which histidine Tag was not completely cleaved in purification.

From the above results, it is considered that the recombinant erythrose reductase obtained in the present Example was expressed in almost the same state as natural type erythrose reductase.

Example 5

Expression of the recombinant erythrose reductase type III using yeast S. cerevisiae was attempted.

(1) Transformation

The erythrose reductase type III cDNA was ligated to a plasmid vector for S. cerevisiae, pYES2/NT (produced by INVITROGEN), said cDNA is obtained by cleaving with BamH I and Xho I a protein expression vector pRSET A for *E. coli* used for expression of the erythrose reductase type III gene in Example 1 (8).

The plasmid vector to which the erythrose reductase type III was ligated was transformed to *E. coli* DH5(to acquire a transformant having acquired Ampicillin resistance.

This transformed *E. coli* cells were cultivated at 37° C. using an LB culture medium containing Ampicillin at a concentration of 50 μg/mL to amplify the plasmid vector to which the erythrose reductase type III cDNA was ligated together with *E. coli*. The plasmid vector was taken out from this *E. coli*, and purification was carried out.

By the lithium acetate method, a vector to which the erythrose reductase type III cDNA was ligated was transformed to a uracil-requiring *S. cerevisiae* INVSc1 strain (produced by INVITROGEN)

Since the strain that acquired the erythrose reductase type III gene achieves synthetic ability of uracil, the strain that acquired the erythrose reductase type III gene was selected by collecting the strain that can grow on a uracil deficient minimal medium described in the experiment manual for a plasmid vector pYES2/NT.

(2) Expression of Protein

Hereinafter, expression of protein was carried out in accordance with the description in the experiment manual for a plasmid vector pYES2/NT produced by INVITROGEN.

Shaking culture of the strain having acquired the erythrose reductase type III gene obtained previously was carried out for 24 hours using 15 mL of a uracil deficient minimal medium containing 2% glucose under the conditions of 30° C. and 220 rpm.

After cultivation, the strain cells were collected by centrifugation (1,500×g, 5 minutes, 4° C.), and this cell was suspended again in 50 mL of a uracil deficient minimal medium containing 2% galactose and 1% raffinose, and then shaking culture was carried out under the conditions of 30° C. and 220 rpm for 48 hours. This culture medium was centrifuged (1,500×g, 5 minutes, 4° C.) to collect the cell.

To about 2 g of this cell, 2 g of 0.5 φmm glass beads were added, and shaking was performed under the condition of 15 seconds×10 times with a shaking cell crusher (B. Braun Melsungen AG) to crush the cell. The cell crushing solution was subjected to centrifugation under the conditions of 12,000×g, 15 minutes and 4° C. to obtain supernatant as a crude enzyme solution.

This crude enzyme solution was treated with Nickel Chelated Agarose in accordance with the method described in Example 1 (8) to purify recombinant erythrose reductase type III from the inside of the cell.

(3) SDS-PAGE

On the purified recombinant erythrose reductase type III expressed in *S. cerevisiae* obtained in (2), SDS-PAGE was carried out using a gel (PAGEL SPG 520L, produced by ATTO CORPORATION).

Figure 10:
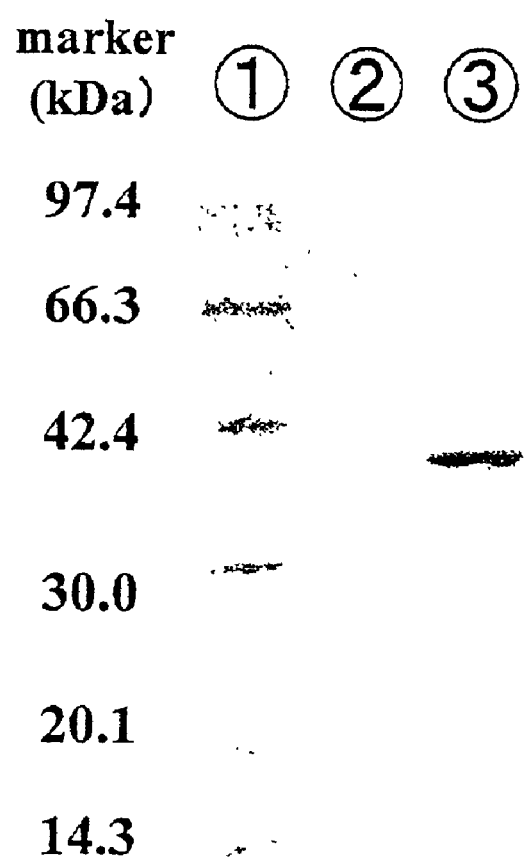
FIG. 10 is an electrophoretogram showing the results of SDS-PAGE on the recombinant erythrose reductase type III, wherein Lane 1 shows the molecular weight marker (kDa), Lane 2 shows the result on the purified recombinant erythrose reductase type III expressed in *S. cerevisiae*, and Lane 3 shows the result on the purified recombinant erythrose reductase type III expressed in *E. coli*.

The results are shown in FIG. 10. In the figure, Lane 1 shows the molecular weight marker (kDa), Lane 2 shows the result on the purified recombinant erythrose reductase type III expressed in *S. cerevisiae*, and Lane 3 shows the result on the purified recombinant erythrose reductase type III expressed in *E. coli*.

As is apparent from Lane 2 in FIG. 10, it was found that the purified recombinant erythrose reductase type III expressed in *S. cerevisiae* could be expressed in the same molecular weight as those of the purified recombinant erythrose reductase type III expressed in *E. coli* and natural type erythrose reductase type III.

(5) Measurement of Enzyme Activity

On the purified recombinant erythrose reductase type III expressed in *S. cerevisiae* obtained in (2), its enzyme activity on erythrose as a substrate was measured under the same conditions as in Example 4(1).

As a result, the specific activity of the enzyme was 19.3 units/mg, and thus the activity was confirmed.

From this result, it was found that the recombinant erythrose reductase type III could be expressed in *S. cerevisiae* in an active state.

What is claimed is:

1. An isolated DNA encoding a protein comprising the amino acid sequence of SEQ ID NO:4.

2. An isolated DNA comprising SEQ ID NO:3.

3. An isolated DNA comprising a polynucleotide which hybridizes under stringent conditions to SEQ ID NO:3, wherein the stringent conditions comprise washing in 2×SSC and 0.1% SDS at 60° C. and wherein the polynucleotide encodes a protein having erythrose reductase type II activity.

4. A host cell transformed with the isolated DNA of claim 1 wherein the isolated DNA encodes a protein having erythrose reductase type II activity.

5. A host cell transformed with the isolated DNA of claim 2 wherein the isolated DNA encodes a protein having erythrose reductase type II activity.

6. A host cell transformed with the isolated DNA of claim 3 wherein the isolated DNA encodes a protein having erythrose reductase type II activity.

7. A method for producing erythrose reductase type II, comprising cultivating the cell of claim 4 in a medium to produce and accumulate erythrose reductase type II in a culture liquid, and separating the erythrose reductase type II from the culture liquid.

8. A method for producing erythrose reductase type II, comprising cultivating the cell of claim 5 in a medium to produce and accumulate erythrose reductase type II in a culture liquid, and separating the erythrose reductase type II from the culture liquid.

9. A method for producing erythrose reductase type II, comprising cultivating the cell of claim 6 in a medium to produce and accumulate erythrose reductase type II in a culture liquid, and separating the erythrose reductase type II from the culture liquid.

10. A method for producing erythritol, comprising contacting the cell as claimed in claim 4 with D-erythrose and harvesting the erythritol produced.

11. A method for producing erythritol, comprising contacting the cell as claimed in claim 5 with D-erythrose and harvesting the erythritol produced.

12. A method for producing erythritol, comprising contacting the cell as claimed in claim 6 with D-erythrose and harvesting the erythritol produced.

* * * * *

SEQUENCE LISTING

```
<160> NUMBER OF SEQ ID NOS: 10

<210> SEQ ID NO 1
<211> LENGTH: 1119
<212> TYPE: DNA
<213> ORGANISM: Trichosporonoides megachiliensis
<220> FEATURE:
<221> NAME/KEY: CDS
<222> LOCATION: (1)..(993)
<223> OTHER INFORMATION:

<400> SEQUENCE: 1 atg tct tac aaa cag tac atc ccc ctg aac gac ggt aac aaa atc cct      48
Met Ser Tyr Lys Gln Tyr Ile Pro Leu Asn Asp Gly Asn Lys Ile Pro
1               5                   10                  15 gcc ctt gga ttt ggt act tgg caa gct gaa cct ggt caa gtg ggt gca      96
Ala Leu Gly Phe Gly Thr Trp Gln Ala Glu Pro Gly Gln Val Gly Ala
            20                  25                  30 agt gtc aag aac gct gtc aag gct ggg tac cgt cat ttg gat ttg gcc     144
Ser Val Lys Asn Ala Val Lys Ala Gly Tyr Arg His Leu Asp Leu Ala
        35                  40                  45
```

```
aaa gtg tac caa aac caa tcg gaa att gga gta gca ctt cag gaa ctg    192
Lys Val Tyr Gln Asn Gln Ser Glu Ile Gly Val Ala Leu Gln Glu Leu
 50                  55                  60 ttt gat caa ggt att gtt aaa cgg gaa gat ttg ttt att acg tcc aaa    240
Phe Asp Gln Gly Ile Val Lys Arg Glu Asp Leu Phe Ile Thr Ser Lys
 65                  70                  75                  80 gta tgg aat aac cgt cat gct cct gaa cat gtt gag cct gca ttg gac    288
Val Trp Asn Asn Arg His Ala Pro Glu His Val Glu Pro Ala Leu Asp
                 85                  90                  95 gaa aca ttg aaa gaa ctt gga ttg tcc tac ttg gat ttg tac ttg att    336
Glu Thr Leu Lys Glu Leu Gly Leu Ser Tyr Leu Asp Leu Tyr Leu Ile
            100                 105                 110 cat tgg ccc gtt gcg ttc aag ttt act acg cct caa gaa cta ttc cct    384
His Trp Pro Val Ala Phe Lys Phe Thr Thr Pro Gln Glu Leu Phe Pro
        115                 120                 125 act gag ccg gat aac aag gaa ttg gcc gcg att gat gat tca atc aag    432
Thr Glu Pro Asp Asn Lys Glu Leu Ala Ala Ile Asp Asp Ser Ile Lys
130                 135                 140 ttg gta gac act tgg aag gca gtt gta gca ctc aaa aaa acg ggt aag    480
Leu Val Asp Thr Trp Lys Ala Val Val Ala Leu Lys Lys Thr Gly Lys
145                 150                 155                 160 acc aaa tcc gtt ggt gtg tcg aac ttc act acg gat ttg gta gac ttg    528
Thr Lys Ser Val Gly Val Ser Asn Phe Thr Thr Asp Leu Val Asp Leu
                165                 170                 175 gtt gaa aaa gcg tcg ggg gaa cga ccg gcg gtc aat cag att gaa gca    576
Val Glu Lys Ala Ser Gly Glu Arg Pro Ala Val Asn Gln Ile Glu Ala
            180                 185                 190 cac cca ttg tta caa cag gat gaa ttg gtt gct cat cac aag agt aaa    624
His Pro Leu Leu Gln Gln Asp Glu Leu Val Ala His His Lys Ser Lys
        195                 200                 205 aac att gtg att act gcg tac agt cct ttg gga aac aat gtg agt ggg    672
Asn Ile Val Ile Thr Ala Tyr Ser Pro Leu Gly Asn Asn Val Ser Gly
210                 215                 220 aaa cca cct ctg act caa aac cct ggg att gaa gca act gcg aaa cgg    720
Lys Pro Pro Leu Thr Gln Asn Pro Gly Ile Glu Ala Thr Ala Lys Arg
225                 230                 235                 240 tta aat cat act cct gct gcg gtc ttg ctt gca tgg ggg att caa cgt    768
Leu Asn His Thr Pro Ala Ala Val Leu Leu Ala Trp Gly Ile Gln Arg
                245                 250                 255 gga tac agt gta ttg gtc aag agt gtt aca cct tct cga att gag agc    816
Gly Tyr Ser Val Leu Val Lys Ser Val Thr Pro Ser Arg Ile Glu Ser
            260                 265                 270 aat tat gat cag att acc ctt tct cct gaa gaa ttc cag aag gtt acg    864
Asn Tyr Asp Gln Ile Thr Leu Ser Pro Glu Glu Phe Gln Lys Val Thr
        275                 280                 285 gat ttg atc aag gaa tat ggc gaa agt cgc aac aat att ccg ttg aat    912
Asp Leu Ile Lys Glu Tyr Gly Glu Ser Arg Asn Asn Ile Pro Leu Asn
290                 295                 300 tat aaa cct tca tgg ccc atc agt gtg ttt ggt aca tcg gat gaa gct    960
Tyr Lys Pro Ser Trp Pro Ile Ser Val Phe Gly Thr Ser Asp Glu Ala
305                 310                 315                 320 aag gct act cat aag att aac acc aac ctt tga gttcagtttg ggaactattt  1013
Lys Ala Thr His Lys Ile Asn Thr Asn Leu
                325                 330 aaagctgctt gctggtcaca ttattgtcag tacctaccat gaagaattca atattatttt  1073
acattgtcaa ccattacatg gatccaaaaa aaaaaaaaaa aaaaaa              1119
```

<210> SEQ ID NO 2
<211> LENGTH: 330

```
<212> TYPE: PRT
<213> ORGANISM: Trichosporonoides megachiliensis

<400> SEQUENCE: 2

Met Ser Tyr Lys Gln Tyr Ile Pro Leu Asn Asp Gly Asn Lys Ile Pro
  1               5                  10                  15

Ala Leu Gly Phe Gly Thr Trp Gln Ala Glu Pro Gly Gln Val Gly Ala
                 20                  25                  30

Ser Val Lys Asn Ala Val Lys Ala Gly Tyr Arg His Leu Asp Leu Ala
             35                  40                  45

Lys Val Tyr Gln Asn Gln Ser Glu Ile Gly Val Ala Leu Gln Glu Leu
         50                  55                  60

Phe Asp Gln Gly Ile Val Lys Arg Glu Asp Leu Phe Ile Thr Ser Lys
 65                  70                  75                  80

Val Trp Asn Asn Arg His Ala Pro Glu His Val Glu Pro Ala Leu Asp
                 85                  90                  95

Glu Thr Leu Lys Glu Leu Gly Leu Ser Tyr Leu Asp Leu Tyr Leu Ile
                100                 105                 110

His Trp Pro Val Ala Phe Lys Phe Thr Thr Pro Gln Glu Leu Phe Pro
            115                 120                 125

Thr Glu Pro Asp Asn Lys Glu Leu Ala Ala Ile Asp Asp Ser Ile Lys
        130                 135                 140

Leu Val Asp Thr Trp Lys Ala Val Val Ala Leu Lys Lys Thr Gly Lys
145                 150                 155                 160

Thr Lys Ser Val Gly Val Ser Asn Phe Thr Thr Asp Leu Val Asp Leu
                165                 170                 175

Val Glu Lys Ala Ser Gly Glu Arg Pro Ala Val Asn Gln Ile Glu Ala
            180                 185                 190

His Pro Leu Leu Gln Gln Asp Glu Leu Val Ala His Lys Ser Lys
        195                 200                 205

Asn Ile Val Ile Thr Ala Tyr Ser Pro Leu Gly Asn Asn Val Ser Gly
        210                 215                 220

Lys Pro Pro Leu Thr Gln Asn Pro Gly Ile Glu Ala Thr Ala Lys Arg
225                 230                 235                 240

Leu Asn His Thr Pro Ala Ala Val Leu Leu Ala Trp Gly Ile Gln Arg
                245                 250                 255

Gly Tyr Ser Val Leu Val Lys Ser Val Thr Pro Ser Arg Ile Glu Ser
            260                 265                 270

Asn Tyr Asp Gln Ile Thr Leu Ser Pro Glu Glu Phe Gln Lys Val Thr
        275                 280                 285

Asp Leu Ile Lys Glu Tyr Gly Glu Ser Arg Asn Asn Ile Pro Leu Asn
        290                 295                 300

Tyr Lys Pro Ser Trp Pro Ile Ser Val Phe Gly Thr Ser Asp Glu Ala
305                 310                 315                 320

Lys Ala Thr His Lys Ile Asn Thr Asn Leu
                325                 330

<210> SEQ ID NO 3
<211> LENGTH: 1077
<212> TYPE: DNA
<213> ORGANISM: Trichosporonoides megachiliensis
<220> FEATURE:
<221> NAME/KEY: CDS
<222> LOCATION: (1)..(987)
<223> OTHER INFORMATION:

<400> SEQUENCE: 3
```

-continued

| | |
|---|---|
| atg tcc tac aac aag aac atc cct ctc aac gac ggt aac tcc att cct<br>Met Ser Tyr Asn Lys Asn Ile Pro Leu Asn Asp Gly Asn Ser Ile Pro<br>1                    5                  10                15 | 48 |
| gct ctt ggg tac ggt acc tgg caa gca gaa cct ggt cag gtc ggt gaa<br>Ala Leu Gly Tyr Gly Thr Trp Gln Ala Glu Pro Gly Gln Val Gly Glu<br>                20                  25                  30 | 96 |
| ggt gtc aag ctc gct gtt aag gct ggc tac cgt cat ttg gac ttg gcc<br>Gly Val Lys Leu Ala Val Lys Ala Gly Tyr Arg His Leu Asp Leu Ala<br>        35                  40                  45 | 144 |
| aaa gta tac cag aac caa acc gag att ggc caa gct ctc aag gaa ctg<br>Lys Val Tyr Gln Asn Gln Thr Glu Ile Gly Gln Ala Leu Lys Glu Leu<br>50                    55                  60 | 192 |
| ttt gat gag ggt gtt gtc aag cgt gag gac ctt ttc atc act tcc aag<br>Phe Asp Glu Gly Val Val Lys Arg Glu Asp Leu Phe Ile Thr Ser Lys<br>65                    70                  75                  80 | 240 |
| ctt tgg aac aac cgc cac gct cct gag cac gtt gag cct gcg ctc gac<br>Leu Trp Asn Asn Arg His Ala Pro Glu His Val Glu Pro Ala Leu Asp<br>                    85                  90                  95 | 288 |
| gag act ctt aag gag ttg ggt cta tcc tat ttg gac ctg tac ttg att<br>Glu Thr Leu Lys Glu Leu Gly Leu Ser Tyr Leu Asp Leu Tyr Leu Ile<br>                100                  105                110 | 336 |
| cac tgg cct gtt gct ttc aag ttc act act ccc gat gaa ctg ctt cct<br>His Trp Pro Val Ala Phe Lys Phe Thr Thr Pro Asp Glu Leu Leu Pro<br>                115                  120                125 | 384 |
| gct gac cct acc aac aag gac ctt gcc tac att gac gat tcg gtc aaa<br>Ala Asp Pro Thr Asn Lys Asp Leu Ala Tyr Ile Asp Asp Ser Val Lys<br>130                    135                  140 | 432 |
| ttg tcc gac acc tgg aag gcg gtc gtc gcc ctg aaa aag acg ggt aag<br>Leu Ser Asp Thr Trp Lys Ala Val Val Ala Leu Lys Lys Thr Gly Lys<br>145                    150                  155                160 | 480 |
| acc aag tcg gtt ggt gtt tcg aac ttc agc act cgt ctg gtc gac ttg<br>Thr Lys Ser Val Gly Val Ser Asn Phe Ser Thr Arg Leu Val Asp Leu<br>                    165                  170                175 | 528 |
| gtt gag gaa gct tcg ggc gaa cgt cct gcg gtt aac cag atc gaa gct<br>Val Glu Glu Ala Ser Gly Glu Arg Pro Ala Val Asn Gln Ile Glu Ala<br>                180                  185                190 | 576 |
| cac ccc ttg ttg caa caa gac gag ttg gtt gct cac cat aag agc aag<br>His Pro Leu Leu Gln Gln Asp Glu Leu Val Ala His His Lys Ser Lys<br>                195                  200                205 | 624 |
| aac att gtc atc act gct tac agt ccc ttg ggc aac aat gtc gct ggt<br>Asn Ile Val Ile Thr Ala Tyr Ser Pro Leu Gly Asn Asn Val Ala Gly<br>210                    215                  220 | 672 |
| aaa cca cct ctg act gag aat ccc ggt att gtg gat gct gct aag cgt<br>Lys Pro Pro Leu Thr Glu Asn Pro Gly Ile Val Asp Ala Ala Lys Arg<br>225                    230                  235                240 | 720 |
| ctg aac cat act cct gct gct gtg ctc att gct tgg ggt att caa cgc<br>Leu Asn His Thr Pro Ala Ala Val Leu Ile Ala Trp Gly Ile Gln Arg<br>                245                  250                255 | 768 |
| ggg tac agc gtc ttg gtc aag tca gtt aca ccc tca cgg att aag agt<br>Gly Tyr Ser Val Leu Val Lys Ser Val Thr Pro Ser Arg Ile Lys Ser<br>                260                  265                270 | 816 |
| aac ttt gaa cag atc act ctg tct gat gag gaa ttc caa cgg gtt acc<br>Asn Phe Glu Gln Ile Thr Leu Ser Asp Glu Glu Phe Gln Arg Val Thr<br>                275                  280                285 | 864 |
| aac ctc atc aag gag tac ggt gag agc cgt aac aac gtt cct ttc aac<br>Asn Leu Ile Lys Glu Tyr Gly Glu Ser Arg Asn Asn Val Pro Phe Asn<br>290                    295                  300 | 912 |
| tac aag cct tcg tgg tct att gac gtc ttt ggt acc cag tac gag gct<br>Tyr Lys Pro Ser Trp Ser Ile Asp Val Phe Gly Thr Gln Tyr Glu Ala | 960 |

```
                305                 310                 315                 320
aag gct acc cac aag att aac gct taa tgtgctctta tacaaaagt                          1007
Lys Ala Thr His Lys Ile Asn Ala
                325 cgtttgaacc tgtaatgtgt gaatgttatc ctcattgttg catcatctca tcaaaaaaaa                 1067 aaaaaaaaaa                                                                        1077

<210> SEQ ID NO 4
<211> LENGTH: 328
<212> TYPE: PRT
<213> ORGANISM: Trichosporonoides megachiliensis

<400> SEQUENCE: 4

Met Ser Tyr Asn Lys Asn Ile Pro Leu Asn Asp Gly Asn Ser Ile Pro
1               5                   10                  15

Ala Leu Gly Tyr Gly Thr Trp Gln Ala Glu Pro Gly Gln Val Gly Glu
            20                  25                  30

Gly Val Lys Leu Ala Val Lys Ala Gly Tyr Arg His Leu Asp Leu Ala
        35                  40                  45

Lys Val Tyr Gln Asn Gln Thr Glu Ile Gly Gln Ala Leu Lys Glu Leu
    50                  55                  60

Phe Asp Glu Gly Val Val Lys Arg Glu Asp Leu Phe Ile Thr Ser Lys
65                  70                  75                  80

Leu Trp Asn Asn Arg His Ala Pro Glu His Val Glu Pro Ala Leu Asp
                85                  90                  95

Glu Thr Leu Lys Glu Leu Gly Leu Ser Tyr Leu Asp Leu Tyr Leu Ile
            100                 105                 110

His Trp Pro Val Ala Phe Lys Phe Thr Thr Pro Asp Glu Leu Leu Pro
        115                 120                 125

Ala Asp Pro Thr Asn Lys Asp Leu Ala Tyr Ile Asp Asp Ser Val Lys
    130                 135                 140

Leu Ser Asp Thr Trp Lys Ala Val Val Ala Leu Lys Lys Thr Gly Lys
145                 150                 155                 160

Thr Lys Ser Val Gly Val Ser Asn Phe Ser Thr Arg Leu Val Asp Leu
                165                 170                 175

Val Glu Glu Ala Ser Gly Glu Arg Pro Ala Val Asn Gln Ile Glu Ala
            180                 185                 190

His Pro Leu Leu Gln Gln Asp Glu Leu Val Ala His Lys Ser Lys
        195                 200                 205

Asn Ile Val Ile Thr Ala Tyr Ser Pro Leu Gly Asn Asn Val Ala Gly
    210                 215                 220

Lys Pro Pro Leu Thr Glu Asn Pro Gly Ile Val Asp Ala Ala Lys Arg
225                 230                 235                 240

Leu Asn His Thr Pro Ala Ala Val Leu Ile Ala Trp Gly Ile Gln Arg
                245                 250                 255

Gly Tyr Ser Val Leu Val Lys Ser Val Thr Pro Ser Arg Ile Lys Ser
            260                 265                 270

Asn Phe Glu Gln Ile Thr Leu Ser Asp Glu Glu Phe Gln Arg Val Thr
        275                 280                 285

Asn Leu Ile Lys Glu Tyr Gly Glu Ser Arg Asn Asn Val Pro Phe Asn
    290                 295                 300

Tyr Lys Pro Ser Trp Ser Ile Asp Val Phe Gly Thr Gln Tyr Glu Ala
305                 310                 315                 320

Lys Ala Thr His Lys Ile Asn Ala
                325
```

-continued

325

<210> SEQ ID NO 5
<211> LENGTH: 1121
<212> TYPE: DNA
<213> ORGANISM: Trichosporonoides megachiliensis
<220> FEATURE:
<221> NAME/KEY: CDS
<222> LOCATION: (1)..(987)
<223> OTHER INFORMATION:

<400> SEQUENCE: 5

| | | |
|---|---|---|
| atg tcc tac aac aag aac atc cct ctc aac gac ggt aac tcc atc cct<br>Met Ser Tyr Asn Lys Asn Ile Pro Leu Asn Asp Gly Asn Ser Ile Pro<br>1                  5                    10                  15 | 48 |
| gcc ctt ggc tac ggt acc tgg caa gca gaa cct ggt cag gtc ggt gaa<br>Ala Leu Gly Tyr Gly Thr Trp Gln Ala Glu Pro Gly Gln Val Gly Glu<br>                  20                    25                    30 | 96 |
| ggt gtc aag ctc gct gtc aaa gct ggc tac cgt cac ttg gac ttg gcc<br>Gly Val Lys Leu Ala Val Lys Ala Gly Tyr Arg His Leu Asp Leu Ala<br>           35                    40                    45 | 144 |
| aaa gtt tac cag aac caa acc gag att ggc caa gct ctc aag gaa ctg<br>Lys Val Tyr Gln Asn Gln Thr Glu Ile Gly Gln Ala Leu Lys Glu Leu<br>50                    55                    60 | 192 |
| ttt gat gag ggt gtt gtc aag cgt gag gac ctt ttc atc act tcc aag<br>Phe Asp Glu Gly Val Val Lys Arg Glu Asp Leu Phe Ile Thr Ser Lys<br>65                    70                    75                    80 | 240 |
| ctt tgg aac aac cgc cac gct cct gag cac gtt gag cct gcg ctc gac<br>Leu Trp Asn Asn Arg His Ala Pro Glu His Val Glu Pro Ala Leu Asp<br>                  85                    90                    95 | 288 |
| gag act ctt aag gag ctg ggt cta tcc tat ctg gac ctg tac ttg att<br>Glu Thr Leu Lys Glu Leu Gly Leu Ser Tyr Leu Asp Leu Tyr Leu Ile<br>           100                    105                 110 | 336 |
| cac tgg cct gtt gct ttc aag ttc act act ccc gat gaa ttg ctc cct<br>His Trp Pro Val Ala Phe Lys Phe Thr Thr Pro Asp Glu Leu Leu Pro<br>           115                    120                 125 | 384 |
| gct gac cct acc aac aag gat ctt gcc tac gtt gac gat tcg gta aaa<br>Ala Asp Pro Thr Asn Lys Asp Leu Ala Tyr Val Asp Asp Ser Val Lys<br>130                    135                    140 | 432 |
| ttg tcc gac acc tgg aag gcg gtc gtc gcc ctg aag aag acg ggt aag<br>Leu Ser Asp Thr Trp Lys Ala Val Val Ala Leu Lys Lys Thr Gly Lys<br>145                    150                    155                    160 | 480 |
| acc aag tcg gtt ggt gtt tcg aac ttc agc act cgt ctg gtc gac ttg<br>Thr Lys Ser Val Gly Val Ser Asn Phe Ser Thr Arg Leu Val Asp Leu<br>                  165                    170                 175 | 528 |
| gtt gag gaa gct tcg ggc gaa cgt cct gcg gta aac cag atc gaa gct<br>Val Glu Glu Ala Ser Gly Glu Arg Pro Ala Val Asn Gln Ile Glu Ala<br>           180                    185                 190 | 576 |
| cac ccc ttg ttg caa caa gac gag ttg gtt gct cac cat aag agc aag<br>His Pro Leu Leu Gln Gln Asp Glu Leu Val Ala His His Lys Ser Lys<br>           195                    200                 205 | 624 |
| aac att gtc atc act gct tac agt ccc ttg ggc aac aat gtc gct ggt<br>Asn Ile Val Ile Thr Ala Tyr Ser Pro Leu Gly Asn Asn Val Ala Gly<br>210                    215                    220 | 672 |
| aaa cca cct ctg act gag aac ccc ggt att gtg gat gct gct aag cgt<br>Lys Pro Pro Leu Thr Glu Asn Pro Gly Ile Val Asp Ala Ala Lys Arg<br>225                    230                    235                    240 | 720 |
| ttg aac cat act cct gct gct gtg ctc att gct tgg ggt att caa cgc<br>Leu Asn His Thr Pro Ala Ala Val Leu Ile Ala Trp Gly Ile Gln Arg<br>           245                    250                 255 | 768 |
| ggg tac agc gtc ttg gtc aag tca gtt aca ccc tca cgg atc aag agt | 816 |

```
Gly Tyr Ser Val Leu Val Lys Ser Val Thr Pro Ser Arg Ile Lys Ser
            260                 265                 270 aac ttt gaa cag atc act ctg tct gat gag gaa ttc caa cgg gtt acc      864
Asn Phe Glu Gln Ile Thr Leu Ser Asp Glu Glu Phe Gln Arg Val Thr
        275                 280                 285 aac ctc atc aag gag tac ggt gag agc cgt aac aac gtt cct ttc aat      912
Asn Leu Ile Lys Glu Tyr Gly Glu Ser Arg Asn Asn Val Pro Phe Asn
290                 295                 300 tac aag cct tcg tgg tcc att gac gtc ttt ggt acc cag gac gag gct      960
Tyr Lys Pro Ser Trp Ser Ile Asp Val Phe Gly Thr Gln Asp Glu Ala
305                 310                 315                 320 aag gct acc cac aag att aac gct taa tgtgctctta tacaaaagt            1007
Lys Ala Thr His Lys Ile Asn Ala
                325 cgtttgaacc tgtaatgtgt gaatgttatc ctcattgttg catcgtctca tcaaaaaaaa   1067 aaaaaaaaaa aaaaaaaaaa aaaaaaaaaa aaaaaaaaaa aaaaaaaaaa aaaa         1121

<210> SEQ ID NO 6
<211> LENGTH: 328
<212> TYPE: PRT
<213> ORGANISM: Trichosporonoides megachiliensis

<400> SEQUENCE: 6

Met Ser Tyr Asn Lys Asn Ile Pro Leu Asn Asp Gly Asn Ser Ile Pro
1               5                   10                  15

Ala Leu Gly Tyr Gly Thr Trp Gln Ala Glu Pro Gly Gln Val Gly Glu
            20                  25                  30

Gly Val Lys Leu Ala Val Lys Ala Gly Tyr Arg His Leu Asp Leu Ala
        35                  40                  45

Lys Val Tyr Gln Asn Gln Thr Glu Ile Gly Gln Ala Leu Lys Glu Leu
    50                  55                  60

Phe Asp Glu Gly Val Val Lys Arg Glu Asp Leu Phe Ile Thr Ser Lys
65                  70                  75                  80

Leu Trp Asn Asn Arg His Ala Pro Glu His Val Glu Pro Ala Leu Asp
                85                  90                  95

Glu Thr Leu Lys Glu Leu Gly Leu Ser Tyr Leu Asp Leu Tyr Leu Ile
            100                 105                 110

His Trp Pro Val Ala Phe Lys Phe Thr Thr Pro Asp Glu Leu Leu Pro
        115                 120                 125

Ala Asp Pro Thr Asn Lys Asp Leu Ala Tyr Val Asp Ser Val Lys
    130                 135                 140

Leu Ser Asp Thr Trp Lys Ala Val Val Ala Leu Lys Lys Thr Gly Lys
145                 150                 155                 160

Thr Lys Ser Val Gly Val Ser Asn Phe Ser Thr Arg Leu Val Asp Leu
                165                 170                 175

Val Glu Glu Ala Ser Gly Glu Arg Pro Ala Val Asn Gln Ile Glu Ala
            180                 185                 190

His Pro Leu Leu Gln Gln Asp Glu Leu Val Ala His Lys Ser Lys
        195                 200                 205

Asn Ile Val Ile Thr Ala Tyr Ser Pro Leu Gly Asn Asn Val Ala Gly
    210                 215                 220

Lys Pro Pro Leu Thr Glu Asn Pro Gly Ile Val Asp Ala Ala Lys Arg
225                 230                 235                 240

Leu Asn His Thr Pro Ala Ala Val Leu Ile Ala Trp Gly Ile Gln Arg
                245                 250                 255
```

```
Gly Tyr Ser Val Leu Val Lys Ser Val Thr Pro Ser Arg Ile Lys Ser
                260                 265                 270

Asn Phe Glu Gln Ile Thr Leu Ser Asp Glu Glu Phe Gln Arg Val Thr
            275                 280                 285

Asn Leu Ile Lys Glu Tyr Gly Glu Ser Arg Asn Asn Val Pro Phe Asn
        290                 295                 300

Tyr Lys Pro Ser Trp Ser Ile Asp Val Phe Gly Thr Gln Asp Glu Ala
305                 310                 315                 320

Lys Ala Thr His Lys Ile Asn Ala
                325

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 7
cargarctnt tygaycaygg                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 8
tgngcytcna tytgrttnac                                                  20

<210> SEQ ID NO 9
<211> LENGTH: 7
<212> TYPE: PRT
<213> ORGANISM: Trichosporonoides megachiliensis

<400> SEQUENCE: 9

Gln Glu Leu Phe Asp Gln Gly
1               5

<210> SEQ ID NO 10
<211> LENGTH: 7
<212> TYPE: PRT
<213> ORGANISM: Trichosporonoides megachiliensis

<400> SEQUENCE: 10

Val Asn Gln Ile Glu Ala His
1               5
```